US012648957B2

(12) United States Patent
Grohar et al.

(10) Patent No.: US 12,648,957 B2

(45) Date of Patent: Jun. 9, 2026

(54) COMPOSITIONS AND METHODS FOR THE TREATMENT OF SWI-SNF MUTANT TUMORS

(71) Applicant: The Children's Hospital of Philadelphia, Philadelphia, PA (US)

(72) Inventors: Patrick J. Grohar, Philadelphia, PA (US); Maggie H. Chasse, Philadelphia, PA (US); Elissa Ann Levine, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 163 days.

(21) Appl. No.: 17/760,712

(22) PCT Filed: Sep. 16, 2020

(86) PCT No.: PCT/US2020/051088

§ 371 (c)(1),
(2) Date: Mar. 15, 2022

(87) PCT Pub. No.: WO2021/055489

PCT Pub. Date: Mar. 25, 2021

(65) Prior Publication Data

US 2022/0296622 A1 Sep. 22, 2022

Related U.S. Application Data

(60) Provisional application No. 62/901,004, filed on Sep. 16, 2019.

(51) Int. Cl.

*A61K 31/704* (2006.01)
*A61K 45/06* (2006.01)
*A61P 35/00* (2006.01)
*G01N 33/575* (2026.01)

(52) U.S. Cl.

CPC ............ *A61K 31/704* (2013.01); *A61K 45/06* (2013.01); *A61P 35/00* (2018.01); *G01N 33/575* (2026.01); *C12Q 2600/158* (2013.01)

(58) Field of Classification Search

CPC ........ A61K 31/704; A61K 45/06; A61P 35/00
See application file for complete search history.

(56) References Cited

U.S. PATENT DOCUMENTS 7,423,008 B2 9/2008 Rohr et al.
8,772,253 B2 7/2014 González et al.
9,447,135 B2 9/2016 Rohr et al.
11,224,609 B2 1/2022 Rohr et al.
11,466,045 B2 10/2022 Thorson et al.
2013/0071482 A1 3/2013 Bae et al.
2013/0101632 A1 4/2013 Scott et al.
2016/0024130 A1 1/2016 Rohr et al.
2019/0083519 A1 3/2019 Rohr et al.
2020/0131218 A1 4/2020 Thorson et al.
2022/0033429 A1 2/2022 Rohr et al.

FOREIGN PATENT DOCUMENTS

EP 2151448 2/2010
EP 2457921 3/2014
WO WO 2014093652 6/2014
WO WO-2017046403 A1 * 3/2017 .............. A61P 35/00
WO WO 2020106357 5/2020
WO WO 2021055489 3/2021

OTHER PUBLICATIONS

Koibuchi et al. Malignant Rhabdoid Tumor of the Breast: A Case Report, 1995, 25, 273-277 (Year: 1995).*
Cecil Textbook of Medicine, 20th Ed, vol. 1, 1997, p. 1004-1010 (Year: 1997).*
Wu et al. Small-molecule inhibitors, immune checkpoint inhibitors, and more: FDA-approved novel therapeutic drugs for solid tumors from 1991 to 2021, 2022, 15, 143 (Year: 2022).*
Litton JK, Burstein HJ, Turner NC. Molecular Testing in Breast Cancer. Am Soc Clin Oncol Educ Book. Jan. 2019;39:e1-e7. doi: 10.1200/EDBK_237715. Epub May 17, 2019. PMID: 31099622. (Year: 2019).*
Kalimuthu SN, Chetty R. Gene of the month: SMARCB1. J Clin Pathol. Jun. 2016;69(6):484-9. doi: 10.1136/jclinpath-2016-203650. Epub Mar. 3, 2016. PMID: 26941181; Pmcid: PMC4914571. (Year: 2016).*
Mimori K, Inoue H, Shiraishi T, Ueo H, Mafune K, Tanaka Y, Mori M. A single-nucleotide polymorphism of SMARCB1 in human breast cancers. Genomics. Sep. 2002;80(3):254-8. doi: 10.1006/geno.2002.6829. PMID: 12213194. (Year: 2002).*
Chassse et al., "Abstract 4643: Mithramycin amplifies the imbalance between the BAF and PRC2 complexes to drive apoptosis in rhabdoid tumor", Cancer Res 78(13_Supplement): 4634, 2018.
Extended European Search Report and Written Opinion for EP Application No. 20865597.7 dated Aug. 7, 2023, 8 pages.
Boulay, G. et al., "Cancer-Specific Retargeting of BAF Complexes by a Prion-like Domain.," *Cell*, 171.1 (2017): 163-178.

(Continued)

*Primary Examiner* — Bruck Kifle
*Assistant Examiner* — Kevin S Martin
(74) *Attorney, Agent, or Firm* — pH IP Law

(57) ABSTRACT

The present disclosure is directed to the use of mithramycin analogues to treat cancers having mutations in the SWI/SNF pathway, such as rhabdoid cancers with mutations in SMARCB1.

12 Claims, 24 Drawing Sheets

Specification includes a Sequence Listing.

(56) References Cited

OTHER PUBLICATIONS

Chasse, M. H. et al., "Abstract 2883: Mithramycin inhibits KDM6A (Utx) and SWI/SNF to induce apoptosis in malignant rhabdoid tumor," *Cancer Res*, 79 (2019).
Chasse, M. H. et al., "SWI/SNF Inhibition Induces Epigenetic Reprogramming and Durable Tumor Regression in Rhabdoid Tumor," 2019, 1 page.
Chasse, M. H. et al., "Direct therapeutic targeting of SWI/SNF induces epigenetic reprogramming and durable tumor regression in rhabdoid tumor," *bioRxiv*, (2019): 1-44.
Erkek, S. et al., "Comprehensive analysis of chromatin states in atypical teratoid/rhabdoid tumor identifies diverging roles for SWI/SNF and Polycomb in gene regulation," *Cancer Cell*, 35.1 (2019): 95-110.
Grohar, P. J. et al., "Identification of an Inhibitor of the EWS-FLI1 Oncogenic Transcription Factor by High-Throughput Screening," *J Nat Cancer Inst*, 103.12 (2011): 962-978.
Harlow, M. L. et al., "Trabectedin Inhibits EWS-FLI1 and Evicts SWI/SNF from Chromatin in a Schedule dependent Manner," *Clin Cancer Res*. 25.11 (2019): 3417-3429.
Kofman S. et al., "Mithramycin in the Treatment of Metastatic Ewing's Sarcoma," *Cancer*, 31 (1973): 889-893.
Michel, B. C. et al., "A non-canonical SWI/SNF complex is a synthetic lethal target in cancers driven by BAF complex perturbation," *Nat Cell Biol*., 20.12 (2018): 1410-1420.
Núñez, L. E. et al., "A Novel Mithramycin Analogue with High Antitumor Activity and Less Toxicity Generated by Combinatorial Biosynthesis," *Journal of Medicinal Chemistry*, 55 (2012): 5813-5825.
Osgood, C. L. et al., "Identification of Mithramycin Analogues with Improved Targeting of the EWS-FL11 Transcription Factor," *Clinical Cancer Research*, 22.16 (2016): 4105- 4118.
PCT International Preliminary Report on Patentability Opinion issued in International Patent Application No. PCT/US2020/051088, dated Mar. 31, 2022.
PCT International Search Report and Written Opinion issued in International Patent Application No. PCT/US2020/051088, dated Feb. 17, 2021.
Selvanathan, S. P. et al., "EWS-FLI1 modulated alternative splicing of ARID1A reveals novel oncogenic function through the BAF complex," *Nucleic Acids Research*, 47.18 (2019): 9619-9636.
Teicher, B. A. et al., "Sarcoma Cell Line Screen of Oncology Drugs and Investigational Agents Identifies Patterns Associated with Gene and microRNA Expression," *Molecular Cancer Therapeutics*, 14.11 (2015): 2452-2462.
Tornin, J. et al., "Inhibition of SP1 by the mithramycin analog EC-8042 efficiently targets tumor initiating cells in sarcoma," *Oncotarget*, 7.21 (2016): 30935-30950.
Wang, X. et al., "BRD9 defines a SWI/SNF sub-complex and constitutes a specific vulnerability in malignant rhabdoid tumors," Nature Communications, 10 (2019): 1-11.
Wang, X. et al., "Oncogenesis caused by loss of the SNF5 tumor suppressor is dependent upon activity of BRG1, the ATPase of the SWI/SNF chromatin remodeling complex," *Cancer Res*., 69.20 (2009): 8094-8101.

* cited by examiner

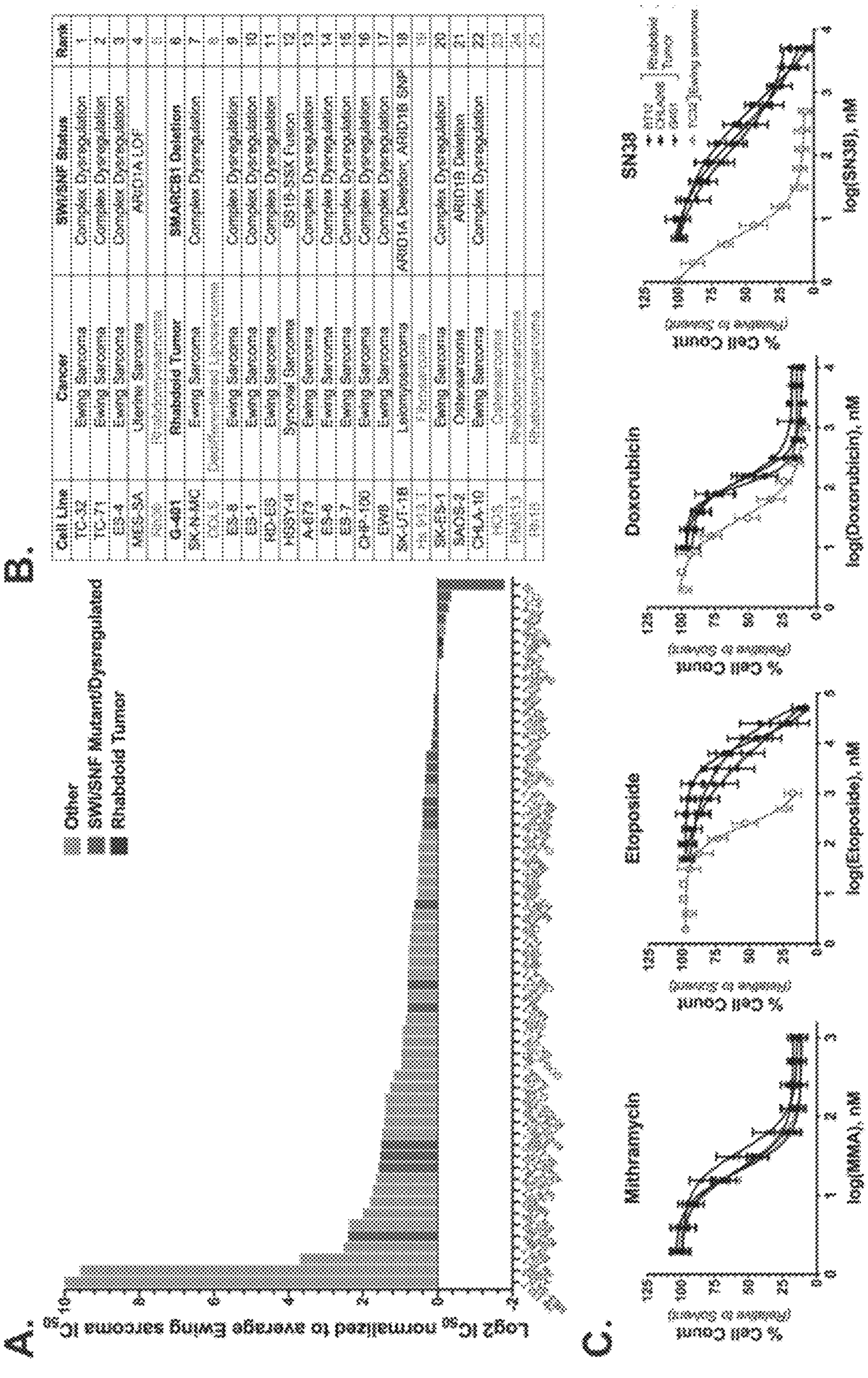
FIGS. 1A-C

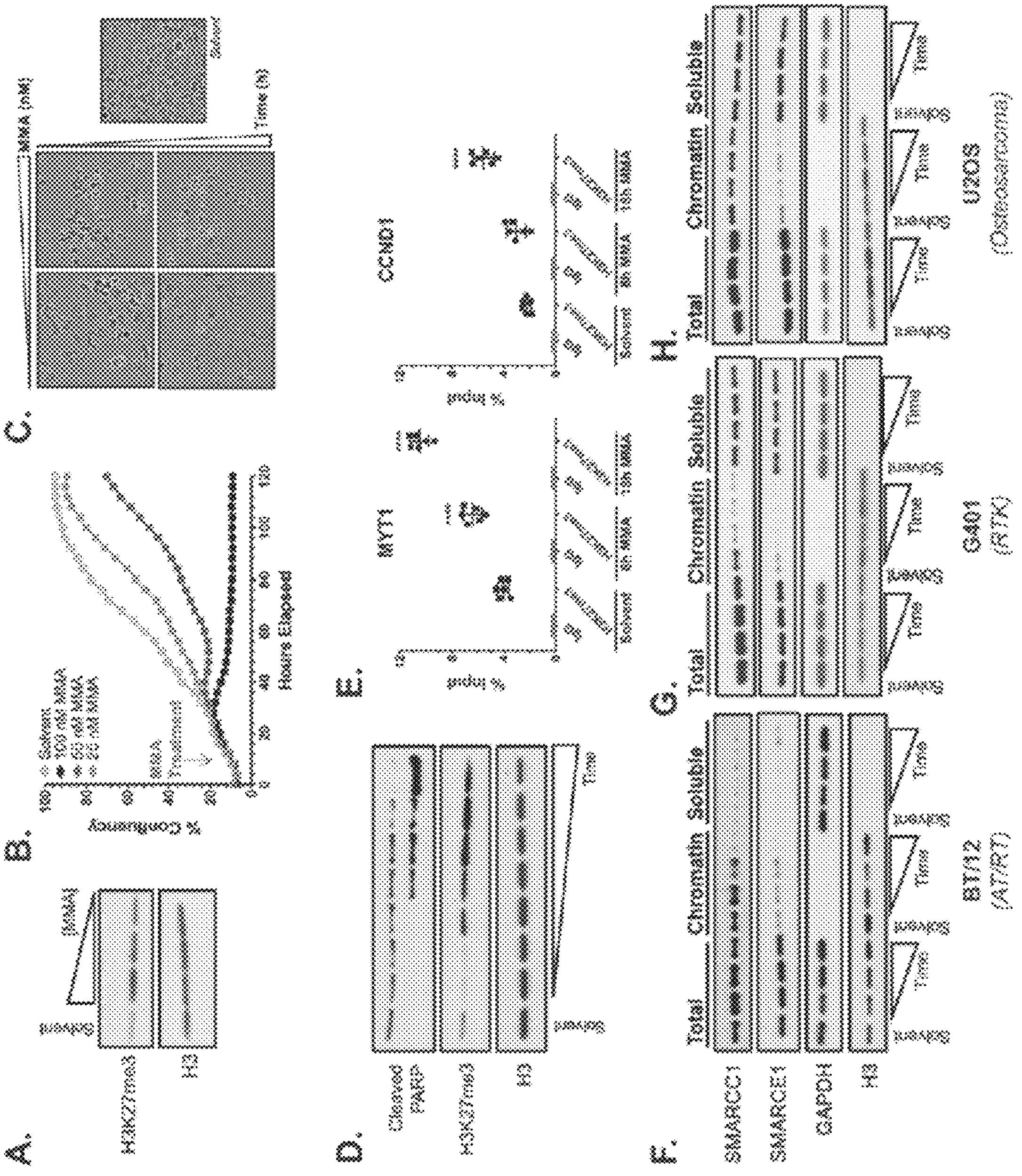
FIGS. 2A-H

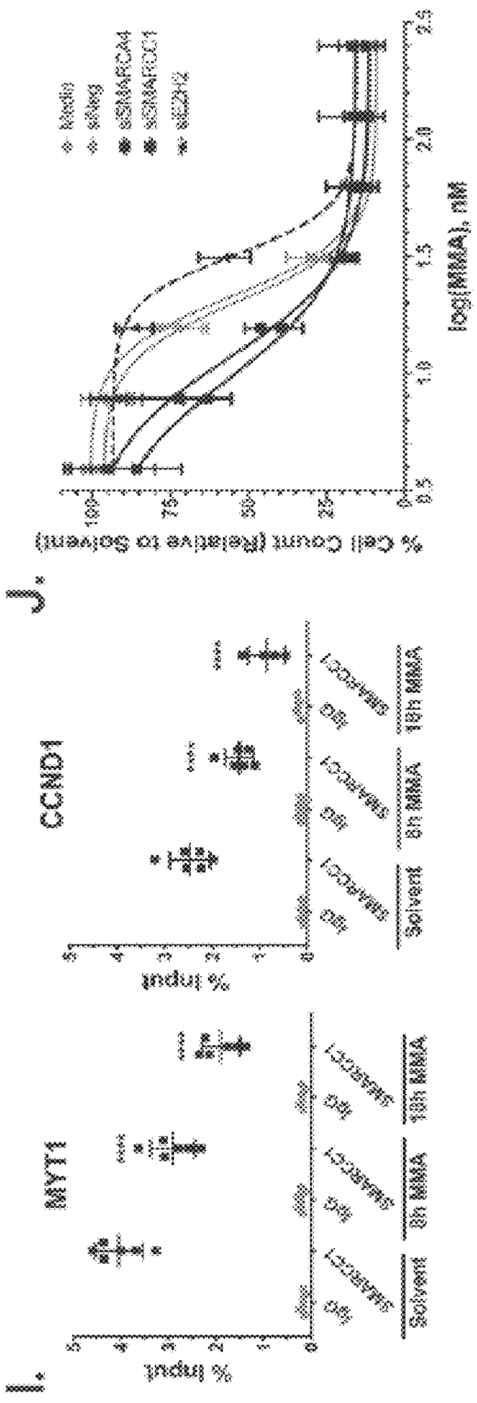
FIGS. 2I-J

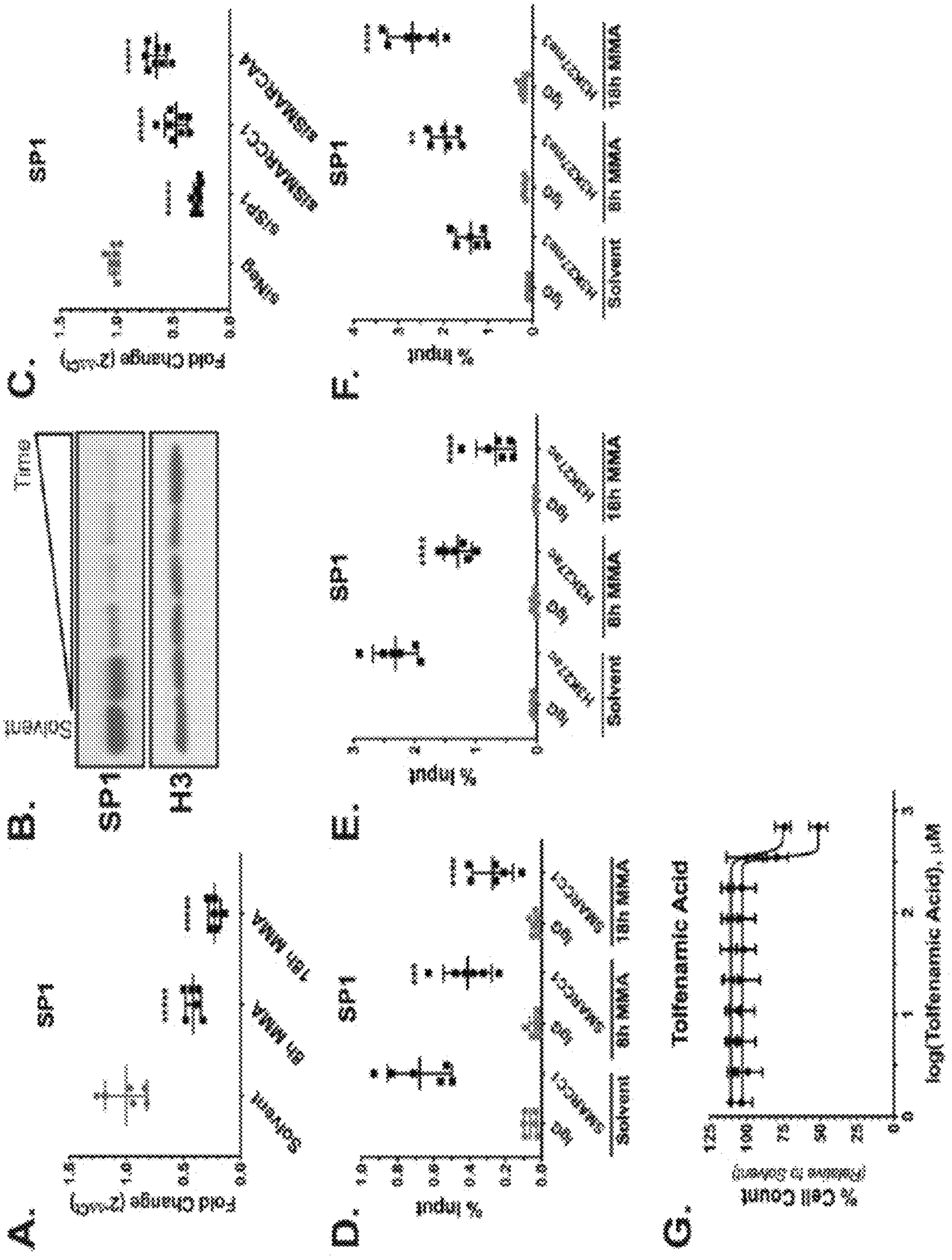
FIGS. 3A-G

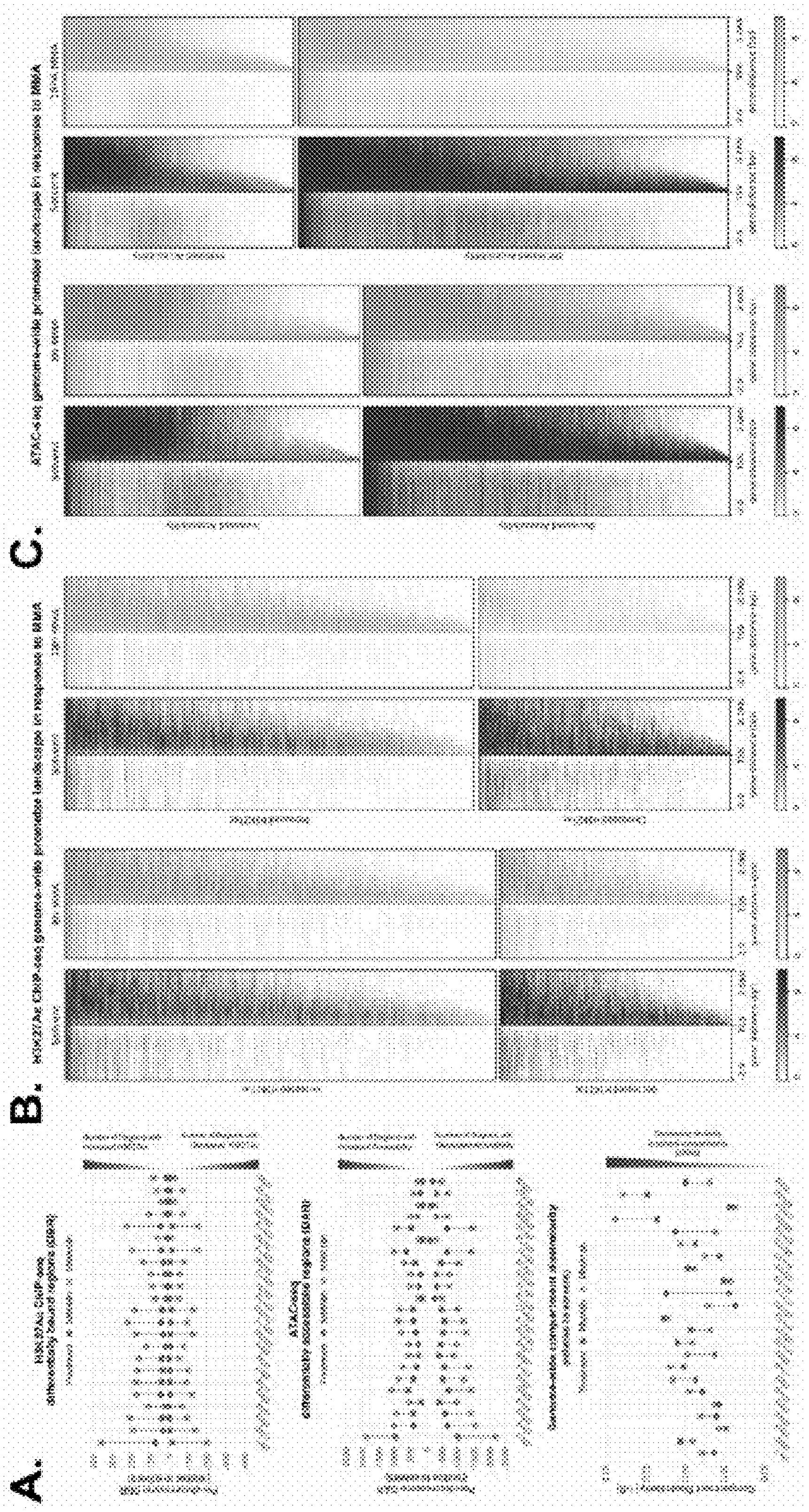
FIGS. 4A-C

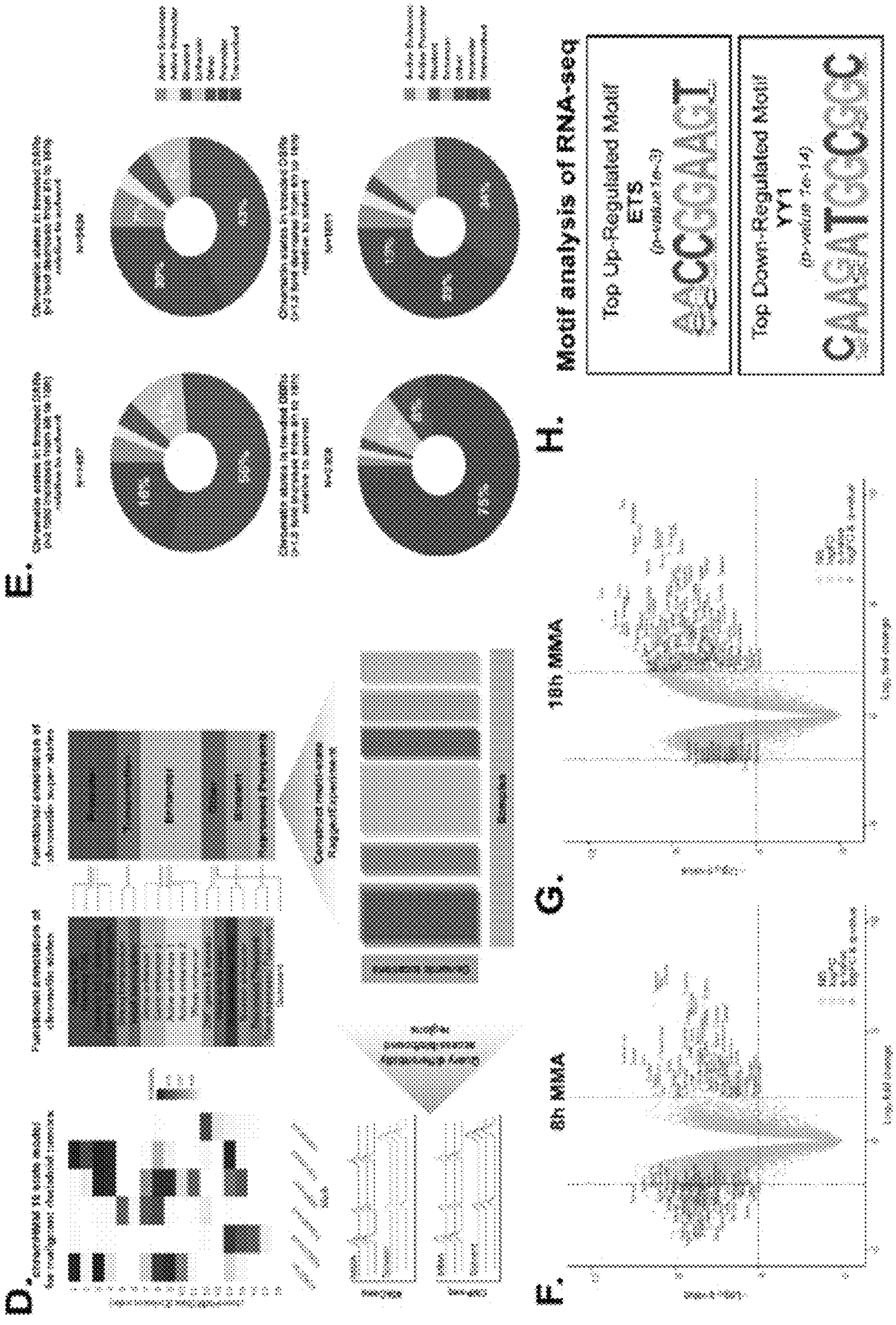
FIGS. 4D-H

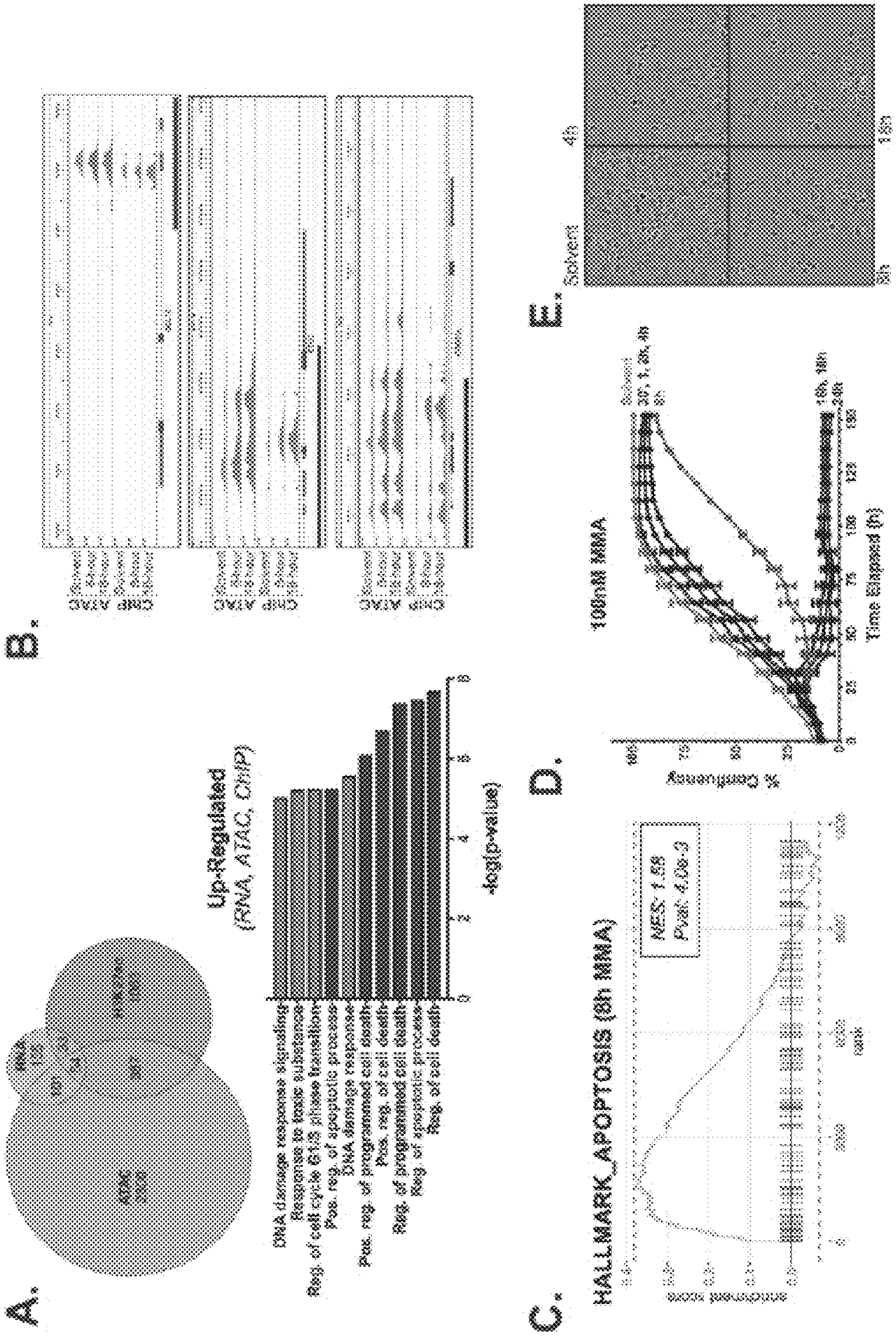
FIGS. 5A-E

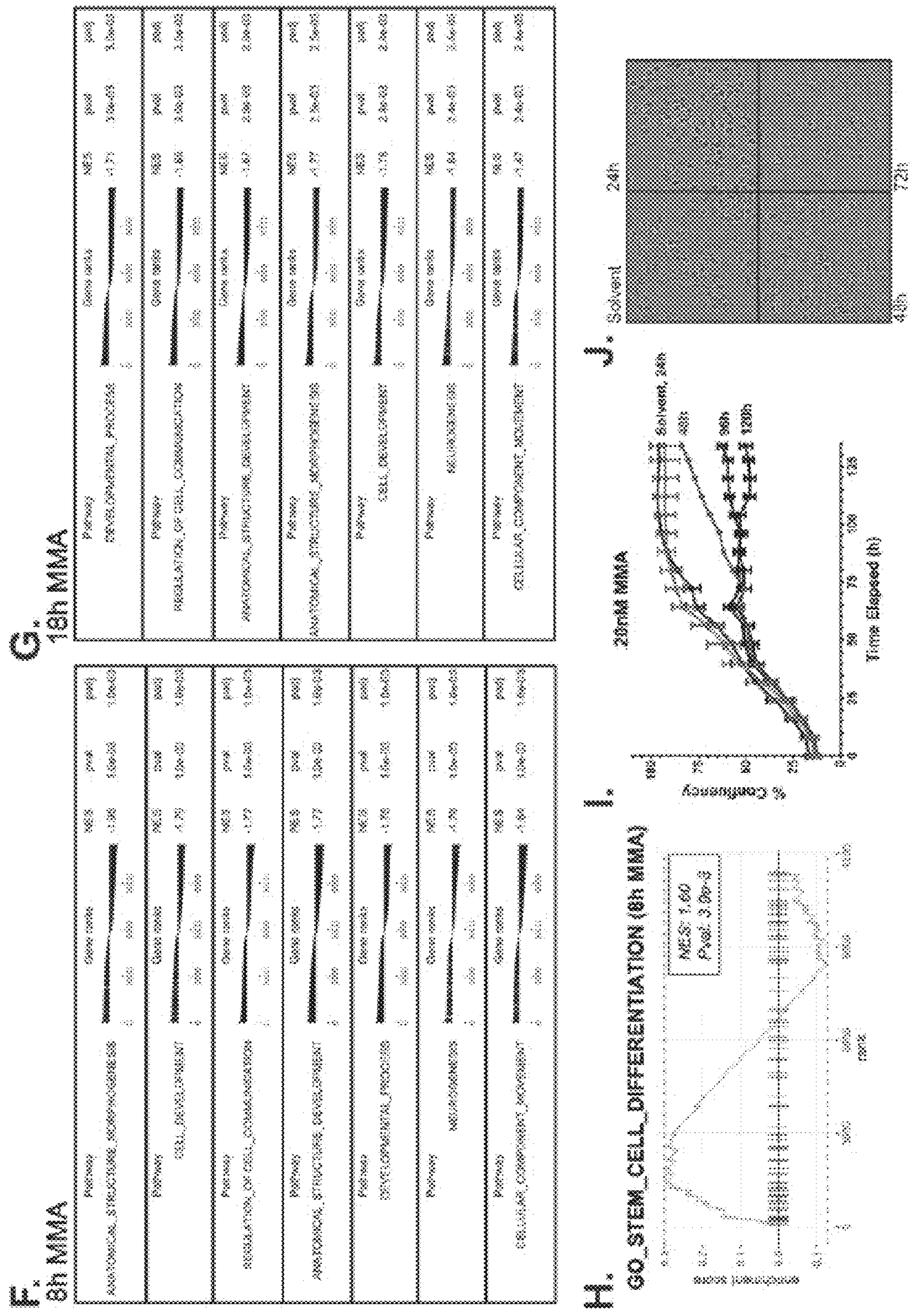
FIGS. 5F-J

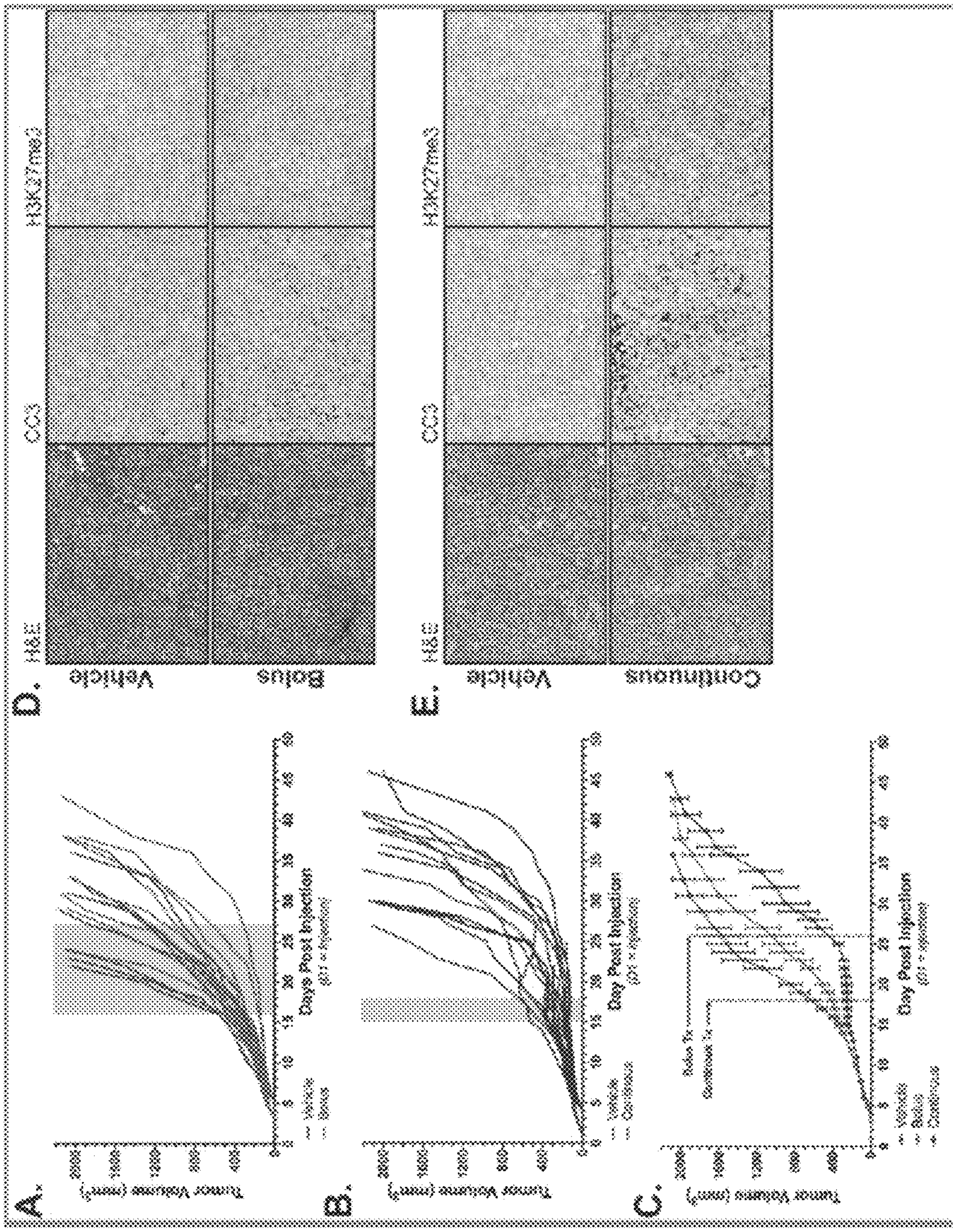
FIGS. 6A-E

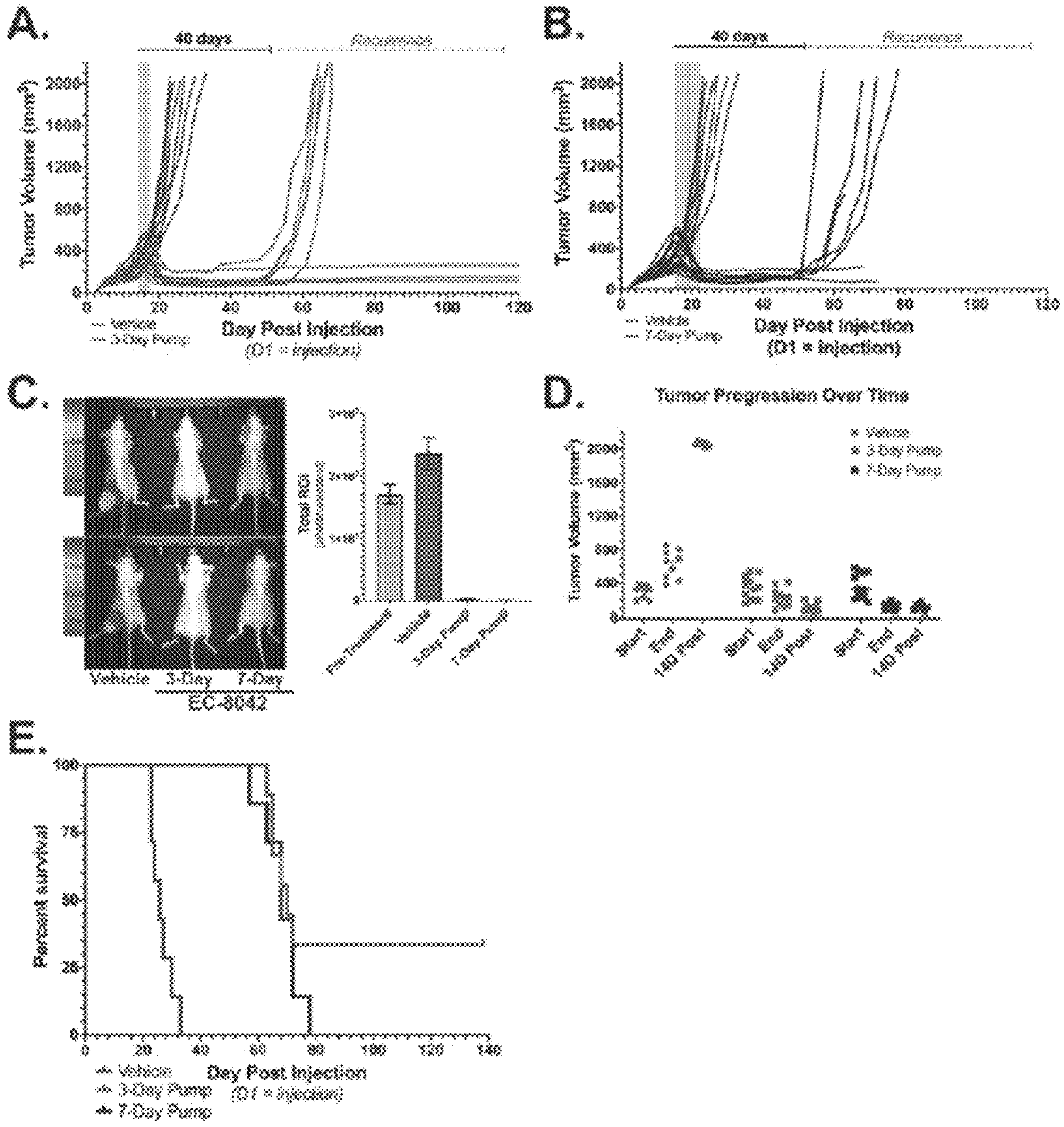
FIGS. 7A-E

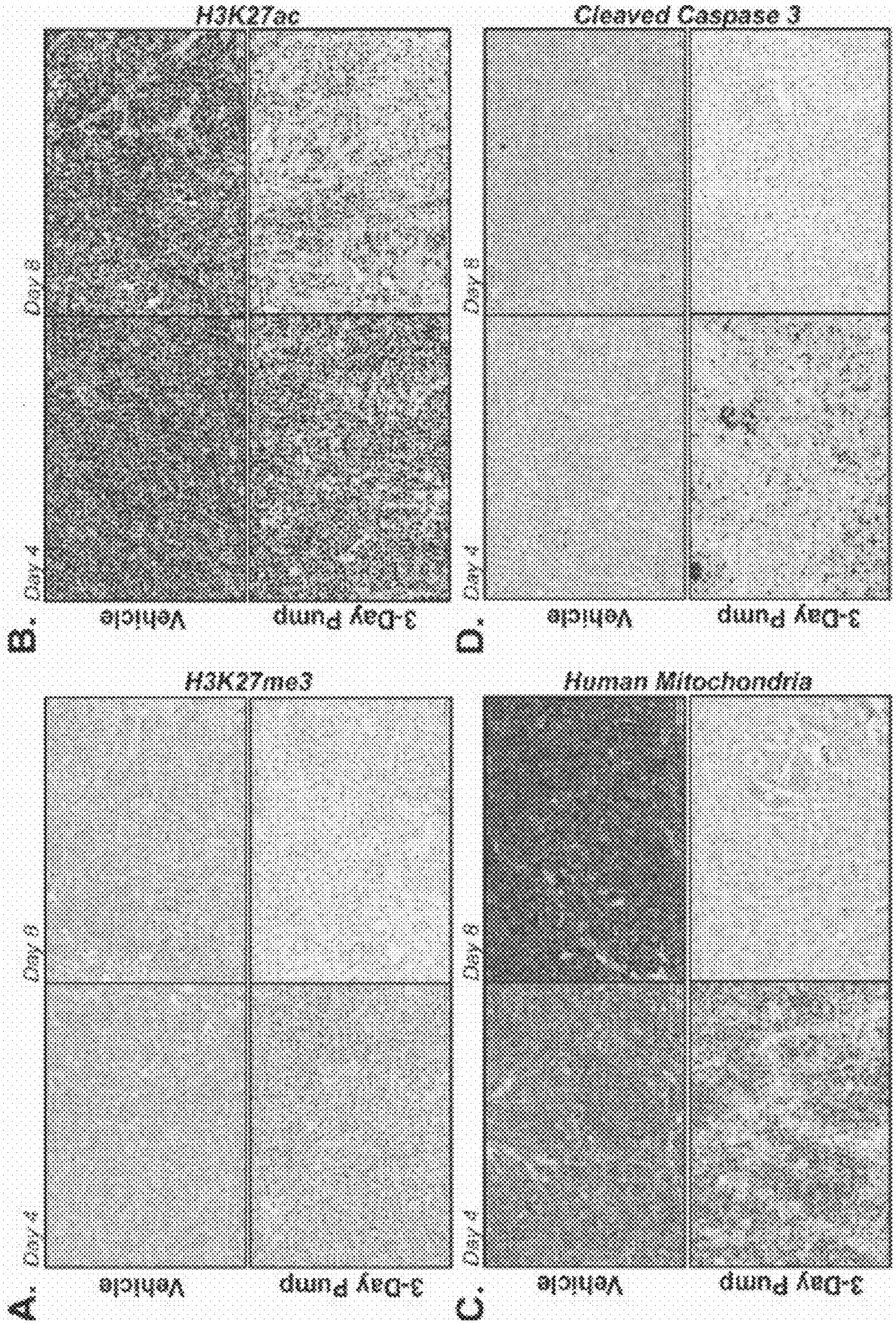
FIGS. 8A-D

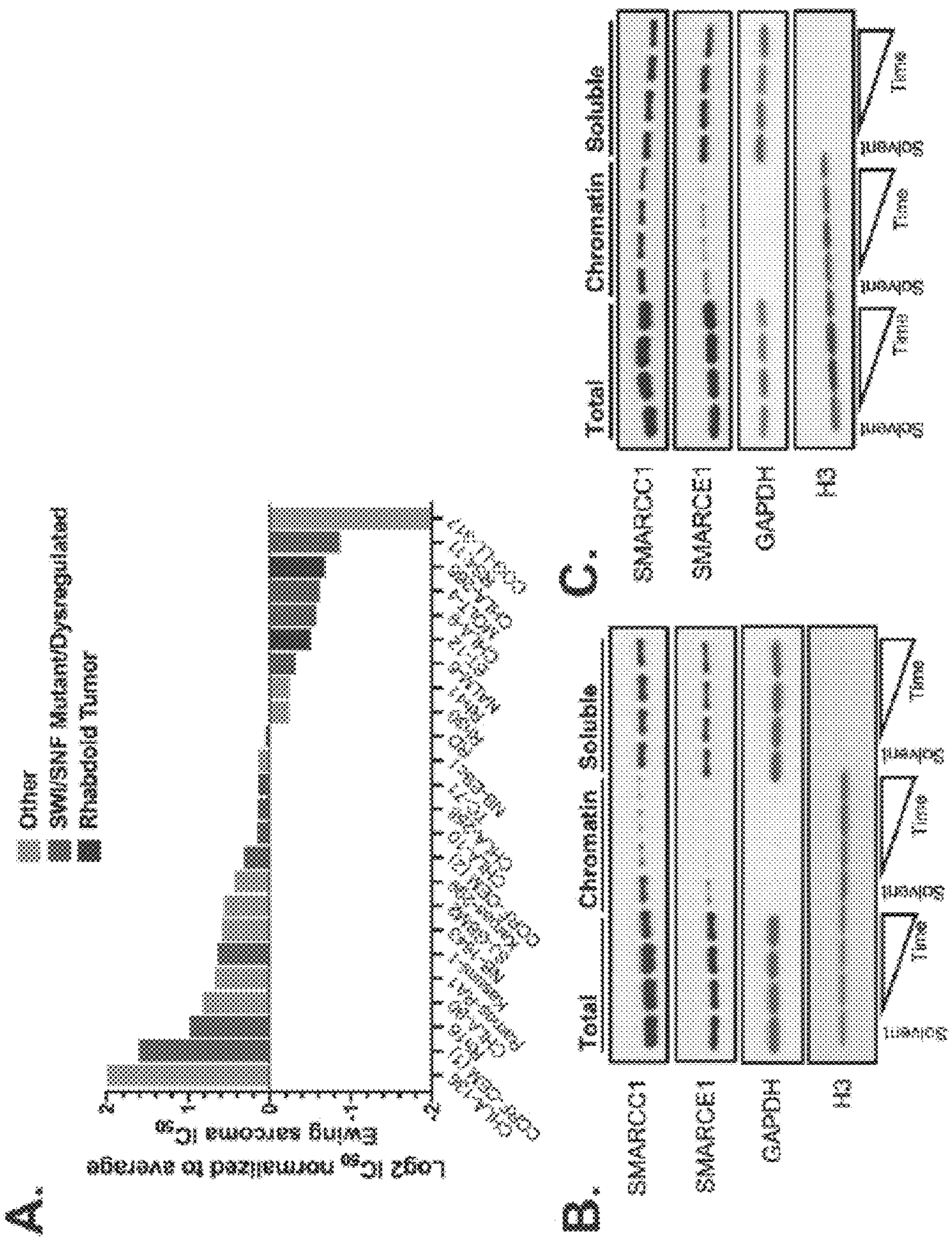
FIGS. S1A-C

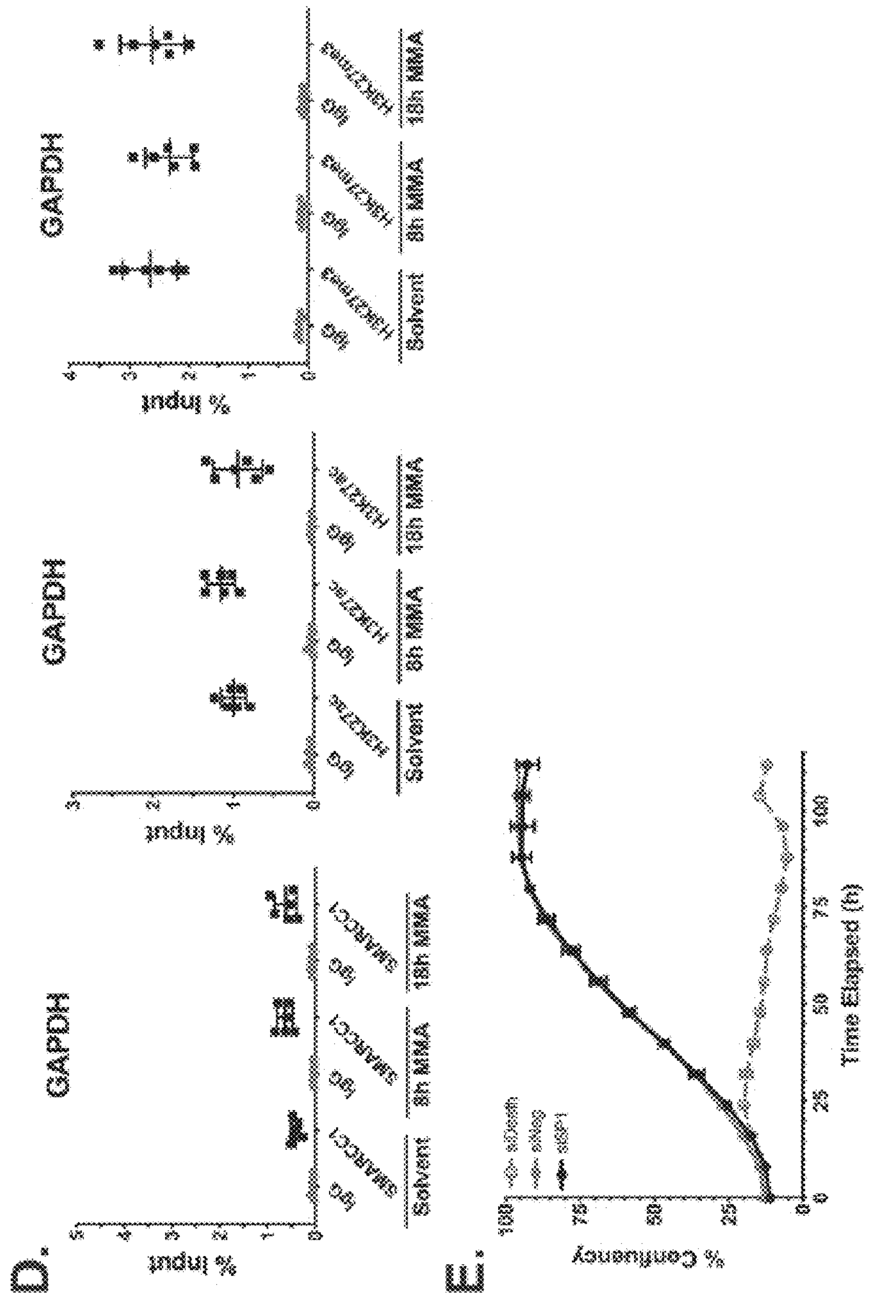
FIGS. S1D-E

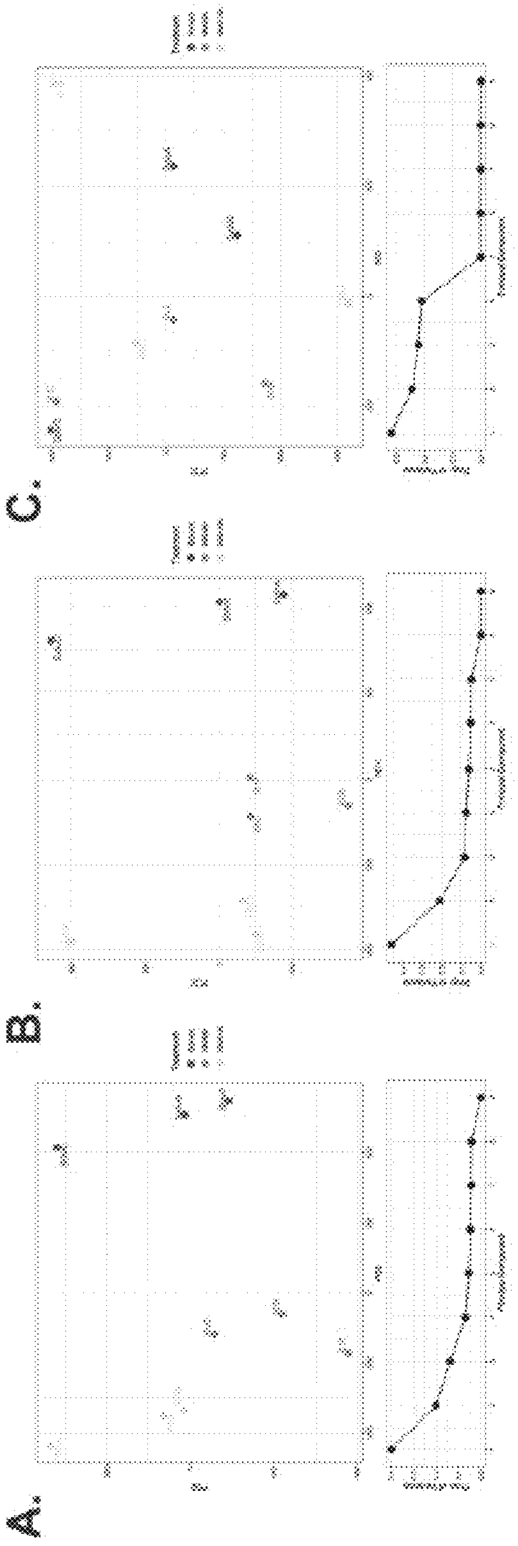
FIGS. S2A-C

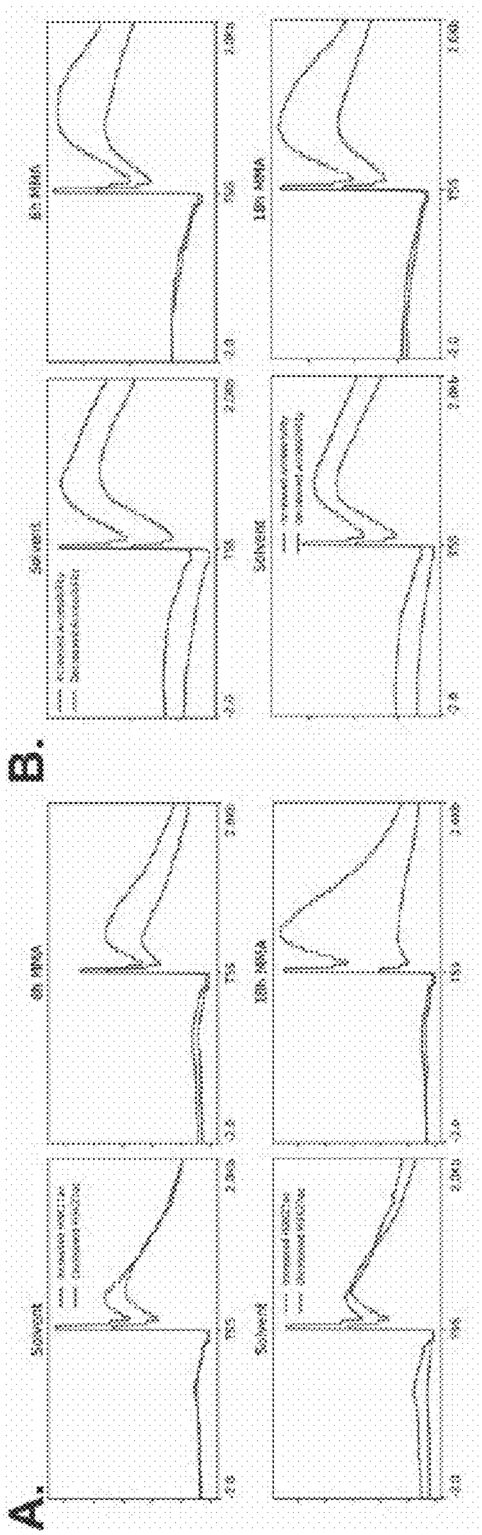
FIGS. S3A-B

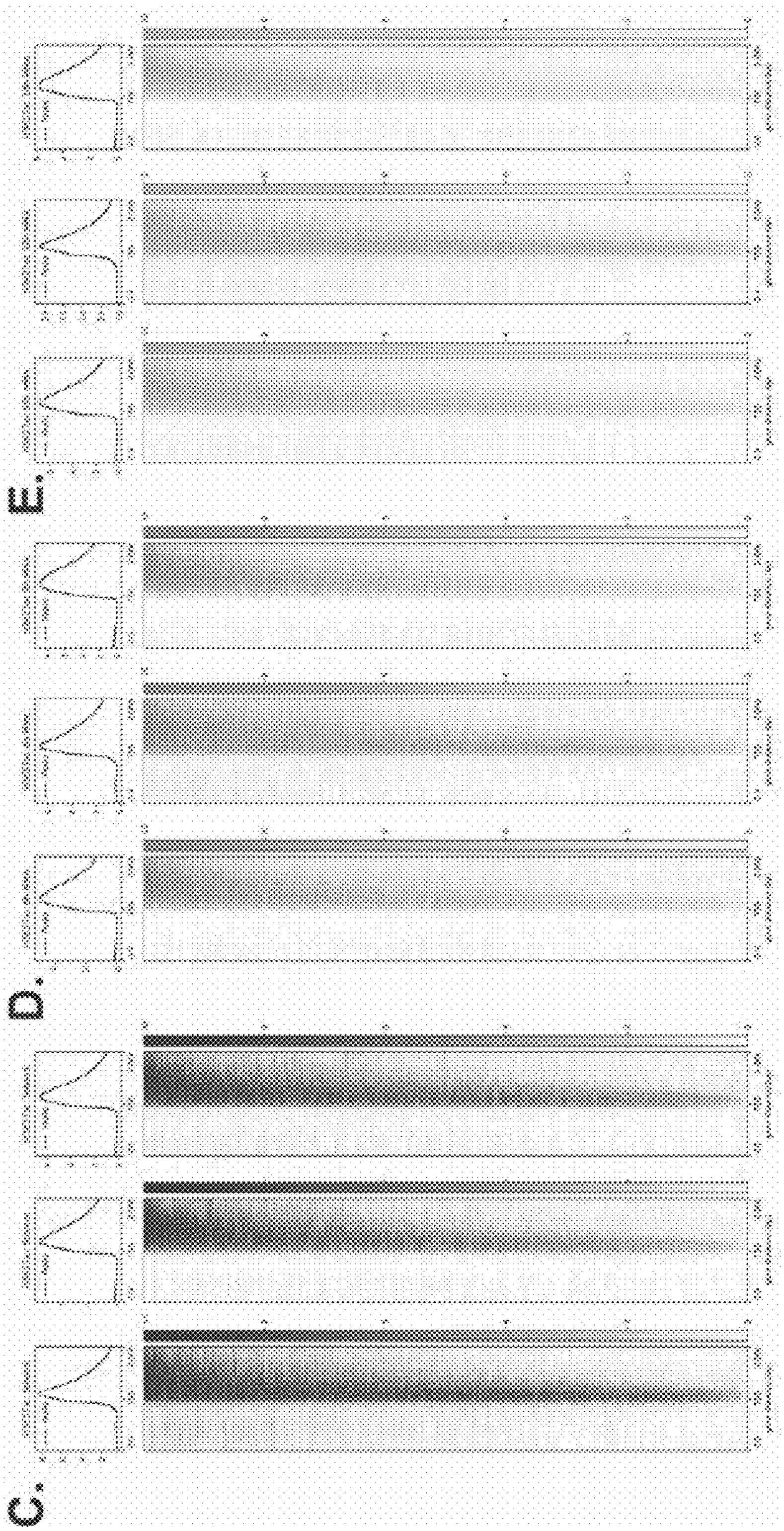
FIGS. S3C-E

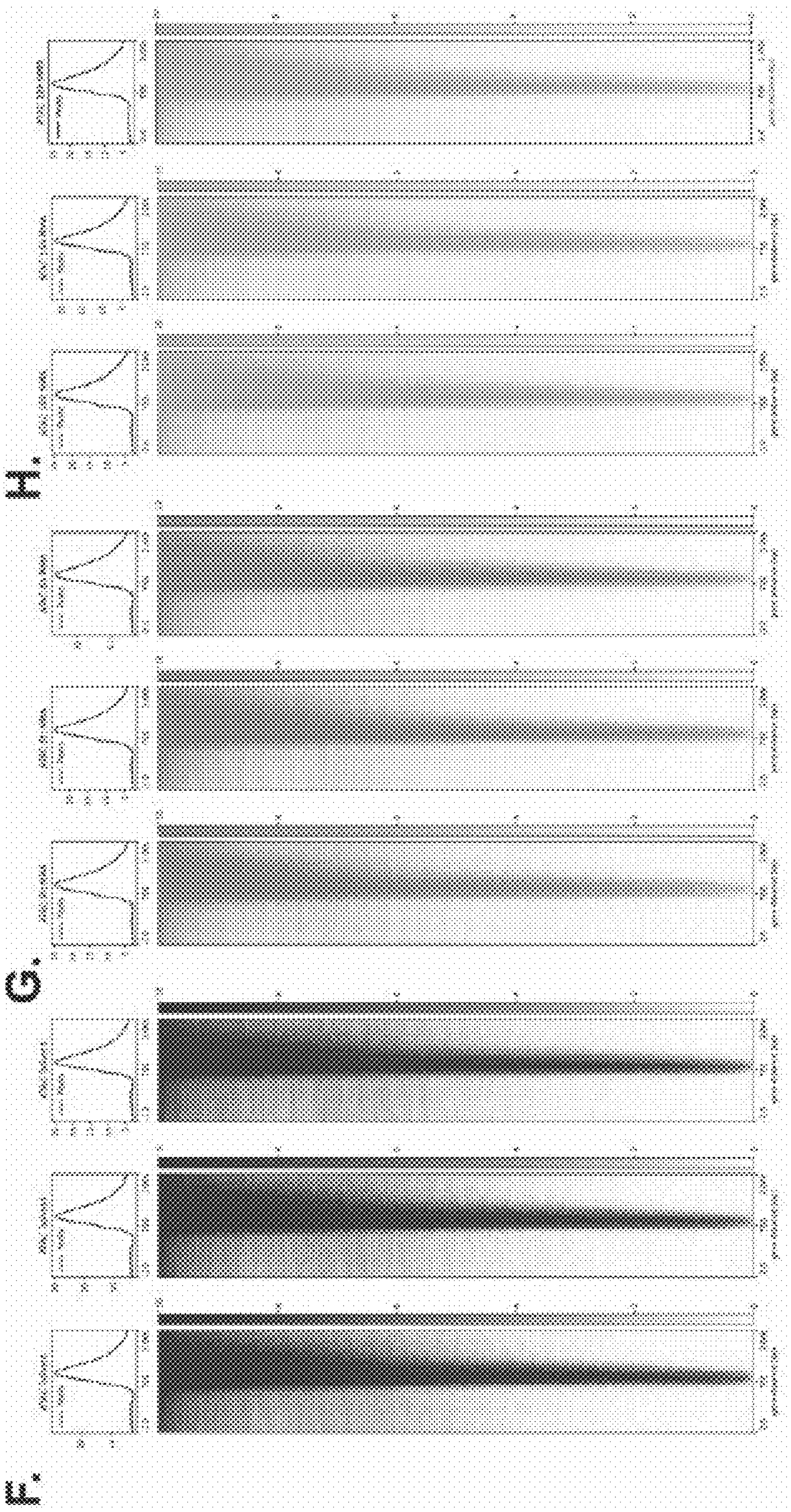
FIGS. S3F-H

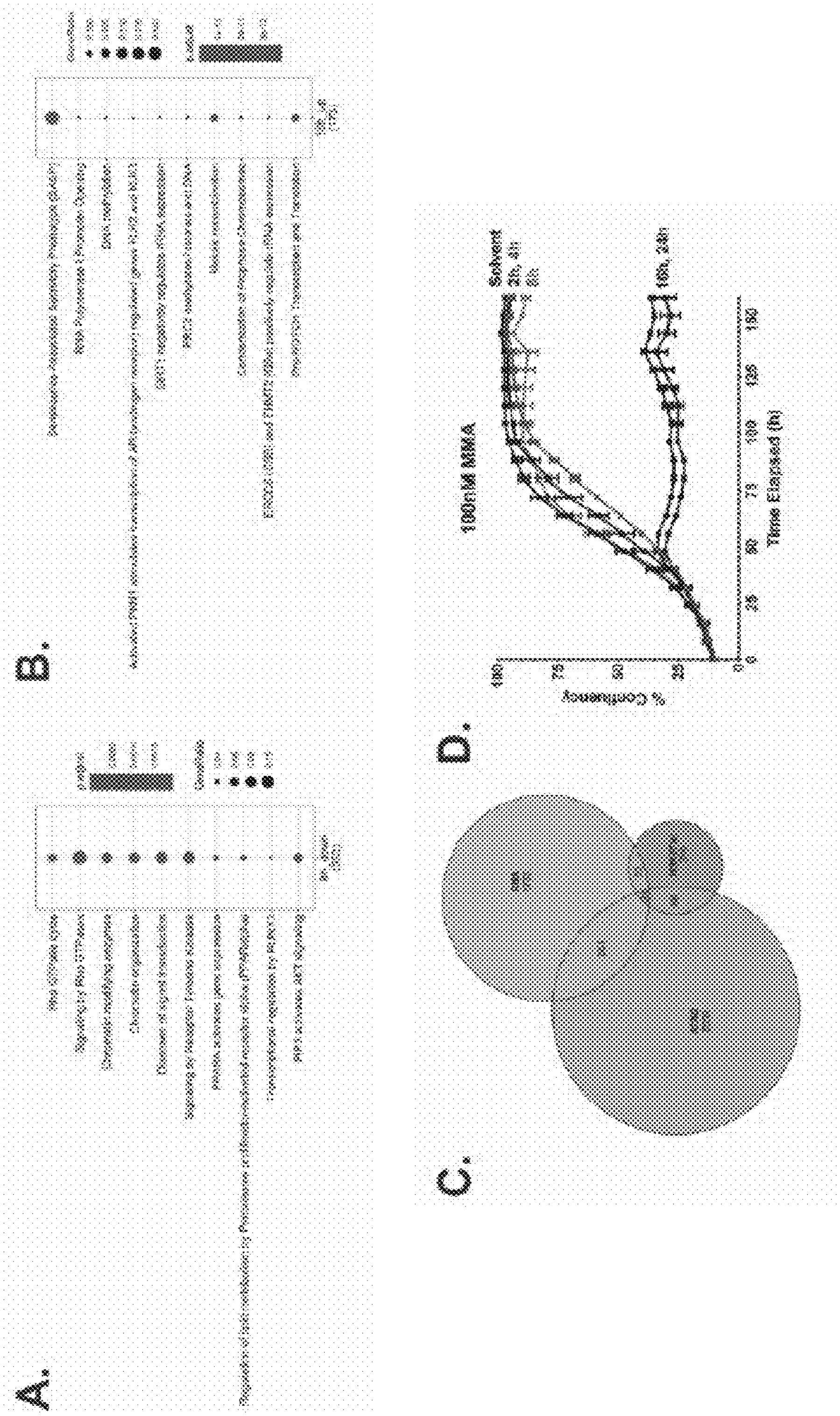
FIGS. S4A-D

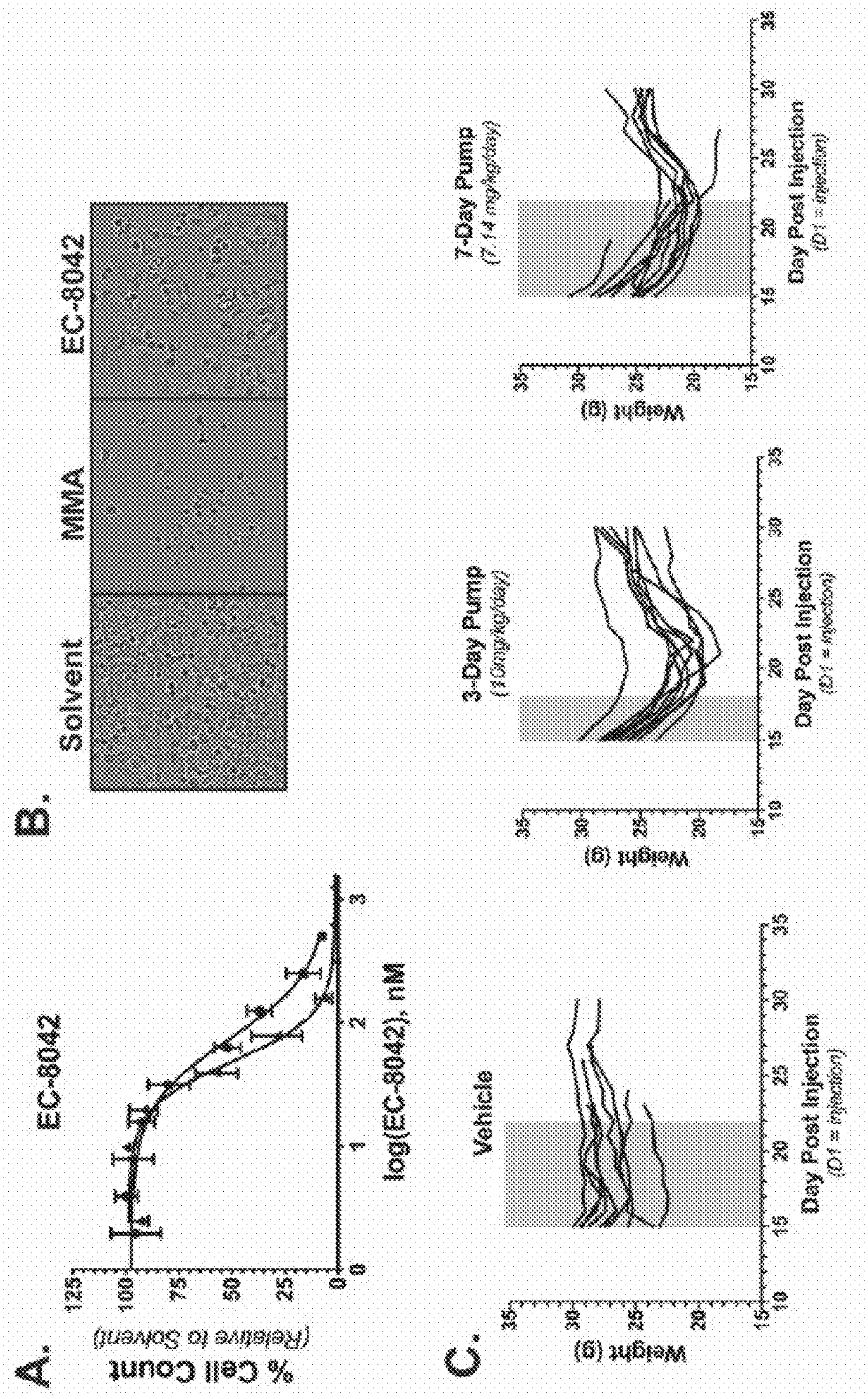
FIGS. S5A-C

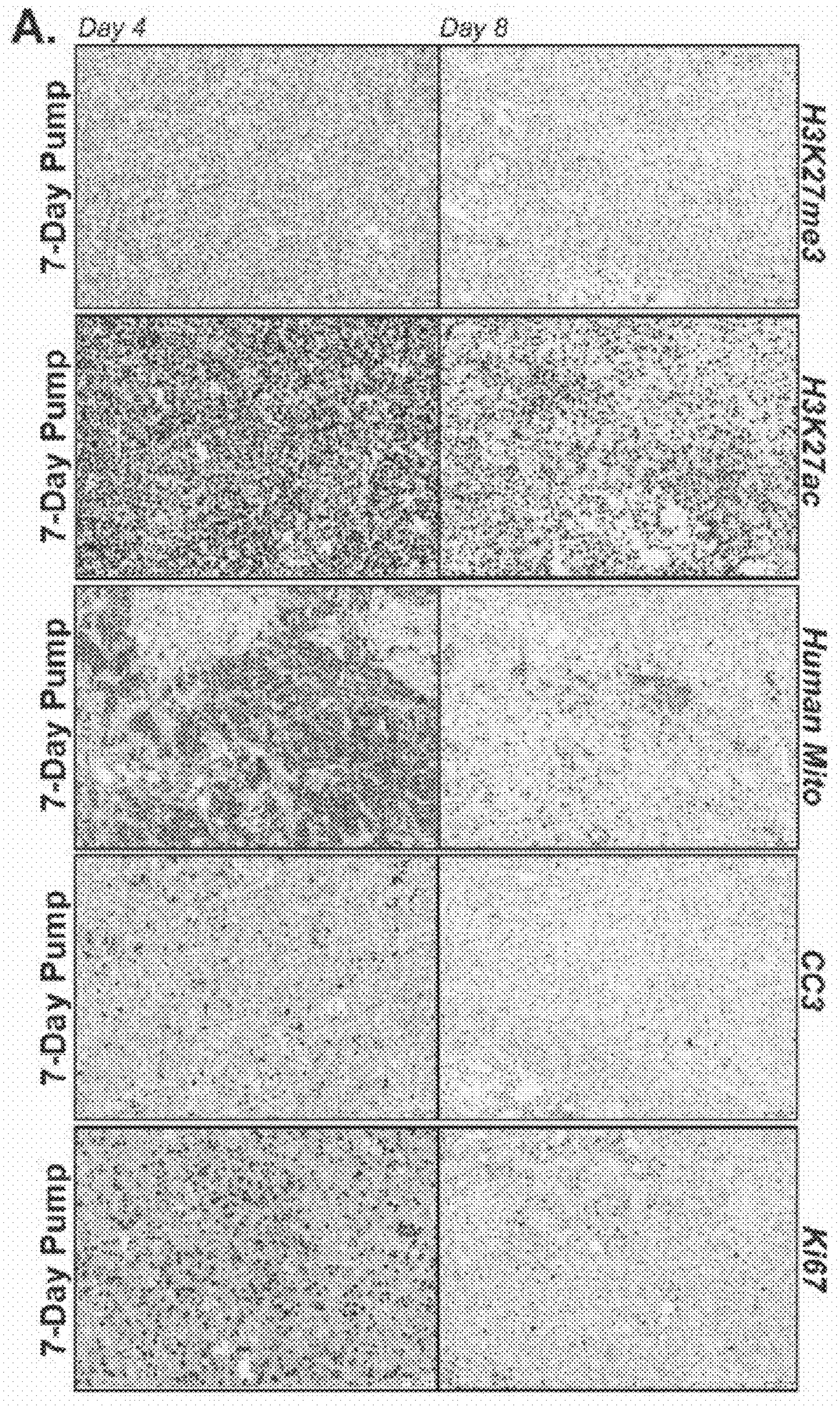
FIG. S6A

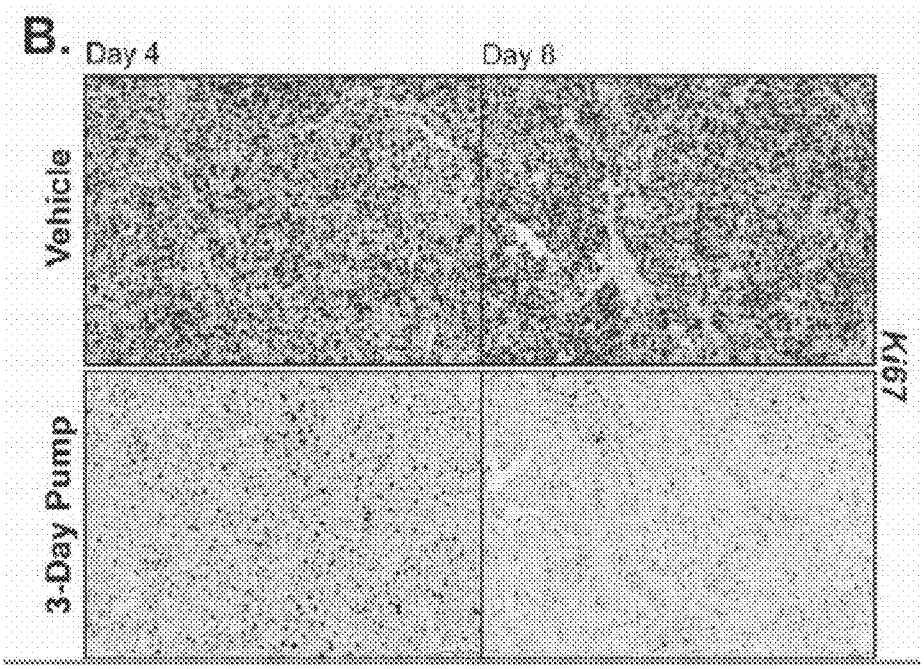
FIGS. S6B

COMPOSITIONS AND METHODS FOR THE TREATMENT OF SWI-SNF MUTANT TUMORS

PRIORITY INFORMATION

This application us a national phase application under 35 U.S.C. § 371 of International Application No. PCT/US2020/051088, filed Sep. 16, 2020, which claims benefit of priority to U.S. Provisional Application Ser. No. 62/901,004, filed Sep. 16, 2019, the entire contents of each of which are hereby incorporated by reference.

REFERENCE TO A SEQUENCE LISTING

The instant application contains a Sequence Listing, which has been submitted in ASCII format via EFS-Web and is hereby incorporated by reference in its entirety. Said ASCII copy, created on May 27, 2025, is named CHOPP0037US_ST25.txt and is 10,550 bytes in size.

BACKGROUND

1. Field

The present disclosure relates generally to the fields of medicine, oncology and genetics. More particularly, it provides methods of treating SWI-SNF mutant cancers, such as rhabdoid tumors, and particularly those having SMARCB1 mutations.

2. Related Art

The SWI/SNF chromatin remodeling complex is mutated in approximately 20% of human cancers. Biallelic inactivation of SMARCB1 (BAF47, INI1, SNF5), and less commonly SMARCA4, is diagnostic of rhabdoid tumor, a pediatric malignancy (Versteege et al., 1998). Rhabdoid tumor can arise in the central nervous system (atypical teratoid rhabdoid tumor, AT/RT), kidney (rhabdoid tumor of the kidney, RTK), or soft-tissues (malignant rhabdoid tumor, MRT) with an overall survival between 20-30% (Brennan, Stiller, & Bourdeaut, 2013; Ginn & Gajjar, 2012).

SMARCB1 deletion promotes tumorigenesis primarily through disruption of polycomb repressive complex (PRC) antagonism. The opposition between SWI/SNF and PRC was first demonstrated in *Drosophila* but has been thoroughly investigated in the context of rhabdoid tumor (Wilson et al., 2010). Here, SMARCB1 loss leads to upregulation of EZH2, the catalytic subunit of PRC2. This upregulation leads to repression of polycomb target genes such as INK4A, a gene required for cell cycle progression (Kia, Gorski, Giannakopoulos, & Verrijzer, 2008). SMARCB1 inactivation does not affect SWI/SNF structural integrity but rather destabilizes the SWI/SNF complex on chromatin (Nakayama et al., 2017). This weakened interaction with chromatin is likely why SMARCB1-loss renders SWI/SNF unable to evict PRC1/2 from chromatin (Kadoch et al., 2017). Due to the antagonistic relationship of SWI/SNF and associated increase in PRC2 activity, EZH2 small molecule inhibition has been proposed as a promising clinical candidate (Knutson et al., 2013).

In addition, to disruption of polycomb repressive complex antagonism, SMARCB1 inactivation dysregulates residual SWI/SNF in rhabdoid tumor. SMARCB1 loss redistributes the residual SWI/SNF complex away from promoters and typical enhancers to occupancy of super enhancers (Wang et al., 2017). SWI/SNF occupancy at super enhancers promotes oncogenesis and blocks differentiation. Specifically, residual SWI/SNF has been shown to occupy cell cycle progression genes such as CDK4 in order to maintain proliferation and knockdown of SWI/SNF subunits with shRNA reduces cellular proliferation (Erkek et al., 2019; Wang et al., 2009). More recent efforts have defined a non-canonical SWI/SNF complex as a synthetic lethal target in rhabdoid tumor (Michel et al., 2018; Wang et al., 2019). Overall, SWI/SNF activity at enhancers and promoters leads to maintenance of oncogenic gene expression programs as well as maintenance of lineage specificity to drive rhabdoid tumor progression. Therefore, as a complementary approach to EZH2 blockade, inhibition of residual SWI/SNF activity is an attractive therapeutic target for the treatment of rhabdoid tumor.

SUMMARY

Thus, in accordance with the present disclosure, there is provided a method of treating a subject having a cancer that exhibits a mutation in the SWI-SNF pathway comprising administering to said subject a mithramycin analogue. The mithramycin analogue may be EC-8042. The method further comprises treating said subject with a second cancer therapy. The second cancer therapy may be chemotherapy, radiotherapy, immunotherapy (e.g., checkpoint inhibitor), hormonal therapy, toxin therapy or surgery. The cancer may exhibit a mutation in SMARCB1. The cancer may be a rhabdoid tumor, such as a malignant rhabdoid tumor, an atypical teratoid rhabdoid tumor or a rhabdoid tumor of the kidney.

The method may further comprise determining, prior to treating, that said subject has an SMARCB1-mutated cancer. Determining may comprise (a) obtaining a sample from said subject that contains protein and/or nucleic acids; and (b) determining mutation status of an SMARCB1 protein (e.g., SEQ ID NO: 1) or nucleic acid encoding SMARCB1 (e.g., SEQ ID NO: 2) in said sample. Determining may comprises a nucleic acid-based assay, or a protein-based assay. The biological sample may be a fluid sample, such as blood, serum plasma, sputum, saliva, urine or nipple aspirate. The biological sample may be a tissue sample, such as a cancer tissue sample.

The subject may be a human subject, such as a pediatric human subject, or a non-human primate. The subject may have previously been diagnosed with cancer, such as a rhabdoid cancer, a SWI/SNF-mutated cancer and/or a SMARCB1-mutated cancer. The cancer may be recurrent, primary, metastatic or multi-drug resistant. The inhibitor of glutamate metabolism may be administered more than once, such as daily, every other day, weekly, monthly and/or on a chronic basis. The inhibitor of glutamate metabolism can be administered continuously, such as with a pump, a patch, via intravenous administration or an intradermal delivery.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-C. Mithramycin cellular sensitivity favors SWI/SNF mutant cancers. (FIG. 1A) Graph of $IC_{50}$ as a function of cell line generated from a published screen of more than 100 agents in 50 sarcoma cell lines (Teicher et al., 2015. Mol Cancer Ther). Cell lines with mutated or dysregulated SWI/SNF (indicated in green) cluster towards the right on the graph indicating these cell lines are more sensitive to mithramycin. (FIG. 1B) Table highlighting the SWI/SNF mutation or dysregulation status in the top 25 sarcoma cell lines from the screen in TA. Mutation status was confirmed in COSMIC or the Achilles dependency map. (FIG. 1C) Dose response curves of rhabdoid tumor and Ewing sarcoma cell lines. Rhabdoid tumor cell lines (black) are sensitive to mithramycin treatment with a similar $IC_{50}$ value as TC32 Ewing sarcoma cells (grey). In contrast, RT cell lines are not sensitive to three chemotherapeutic agents.

FIGS. 2A-J. Mithramycin induced morphological changes are dependent on SWI/SNF eviction and the induction of H3K27me3. (FIG. 2A) Western blot showing dose-dependent increase in H3K27me3 following exposure to 100 nM, 50 nM, 25 nM mithramycin for 18 hours in BT12 cells. (FIG. 2B) Transient exposure of BT12 cells to Mithramycin induces a dose-dependent suppression of proliferation. Cells were exposed to 25 nM, 50 nM, or 100 nM MMA for 18-hours, replaced with drug-free media and monitored for viability using live cell imaging. (FIG. 2C) Exposure of mithramycin induces morphological changes and apoptosis in BT12 cells relative to control cells (solvent). Images are of BT12 cells treated with 25 nM (left) or 100 nM (right) mithramycin for 18-hours (top) or 48-hours (bottom) in the presence of cleaved caspase 3/7 reagent that is green with caspase activation indicative of apoptosis. (FIG. 2D) Mithramycin leads to amplification of H3K27me3 in a time-dependent manner that correlates with the induction of apoptosis as measured by the cleavage of PARP. Western blot lysates collected at 1 h, 2h, 4 h, 8h, 12h 16 h, 18h following continuous 100 nM mithramycin treatment. (FIG. 2E) Chromatin immunoprecipitation qPCR (ChIP-qPCR) of IgG or SMARCC1 at MYT1 and CCND1. H3K27me3 occupancy is increased in a time-dependent manner. (FIGS. 2F-H) Mithramycin evicts SMARCC1 and SMARCE1 SWI/SNF subunits from chromatin in a time-dependent manner in BT12 (FIG. 2F) and G401 (FIG. 2G) cells but not U20S (FIG. 2H) cells. Western blot analysis of biochemical fractionation showing whole cell lysate (total), chromatin bound (chromatin), and nuclear and cytoplasmic soluble (soluble) fractions following exposure to 100 nM mithramycin for 1, 8 or 18 hours and probed for the SWI/SNF subunits (SMARCC1 or SMARCE1) or H3 (chromatin control) and GAPDH (soluble control). (FIG. 2I) Confirmation of loss of SWI/SNF occupancy at defined loci in the genome as measure by ChIP-qPCR at known SWI/SNF target genes, MYT1 and CCND1 vs. an IgG antibody control IgG. (FIG. 2J) Suppression of SWI/SNF subunit expression sensitizes BT12 cells to mithramycin while suppression of EZH2 antagonizes mithramycin activity consistent with the proposed mechanism. Data represents dose response curves of mithramycin in BT12 cells following a 48-hour exposure in the presence of siRNA silencing of the SWI/SNF subunits (SMARCA4 (siSMARCA4) or SMARCC1 (siSMARCC1) relative to untreated cells (Media), a non-targeting siRNA (siNeg) or the PRC2 subunit EZH2 responsible for H3K27me3 (siEZH2).

FIGS. 3A-G. Mithramycin evicts SWI/SNF from the SP1 promoter. (FIG. 3A) SP1 mRNA expression is reduced in a time-dependent manner following 100 nM mithramycin treatment as measured by qPCR fold-change relative to GAPDH ($2^{ddCT}$). **, p-value<0.0001. (FIG. 3B) SP1 protein expression is reduced in a time-dependent manner following 100 nM mithramycin treatment as measured by western blot. Cells were treated with 100 nM mithramycin for 1 h, 4h, 8 h, 12h, 18h. (FIG. 3C) SWI/SNF subunits drive SP1 expression. siRNA knockdown of SMARCC1 and SMARCA4 reduces the mRNA expression of SP1 as measured by qPCR fold-change relative to GAPDH ($2^{ddCT}$). , p-value<0.0001. Cells were treated with siSP1 for 30-hours or siSMARCA4/siSMARCC1 for 48-hours. (FIGS. 3D-F) ChIP-qPCR analysis of SMARCC1 (FIG. 3D), H3K27ac (FIG. 3E), and H3K27me3 (FIG. 3F) occupancy in the SP1 promoter following 8-hours or 18-hours 100 nM mithramycin treatment. SMARCC1 and H3K27ac decrease occupancy in the SP1 promoter while H3K27me3 amplifies following mithramycin treatment. , p-value<0.0001; *, p-value<0.001; , p-value<0.01. (FIG. 3G) Dose response curve of Tolfenamic acid treatment in BT12 (circle) and G401 (triangle) rhabdoid tumor cells. Rhabdoid tumor cells are not sensitive to SP1 degradation. (FIG. 3**H) Western blot analysis confirming concentrations of tolfenamic acid used in 3G degrade active SP1 protein.

FIGS. 4A-H. Mithramycin induces epigenetic reprogramming of chromatin compartments and promoters. (FIG. 4A) Dumbbell plots representing the number of differentially bound (left) or accessible (right) regions changing after mithramycin treatment. (FIG. 4B) Heatmaps showing H3K27ac ChIP-seq differentially bound regions (left) and ATAC-seq differentially accessible regions following 8-hours mithramycin treatment. Peaks were filtered with a 10e-5 q-value threshold. A 2kb window is centered on the TSS. (FIG. 4C) Dumbbell plots representing ATAC-seq chromatin compartments per chromosome following mithramycin treatment (bottom). (FIG. 4D) Schematic for the 18 state chromHMM model built for malignant rhabdoid tumors and collapsed into 6 functional chromatin super states. Chromatin states were called if the state was present in at least 50% of primary samples. ATAC-seq and H3K27ac ChIP-seq peaks were queried against the 6 super states to assign functionality. (FIG. 4E) Donut plots representing the percentage of each chromatin super state across treatment time (from 8h to 18h) that increased 2-fold (left) or decreased 2-fold (right). (FIGS. 4F-G) Volcano plot showing gene expression trends at 8h (F) and 18h (G) MMA treatment. Dashed lines represent a 2 log FC and 10e-5 q-value threshold. (FIG. 4H) Motif analysis of the top up-regulated and down-regulated motifs from the RNA-seq gene lists that pass the log FC and q-value threshold in FIGS. 4F-G.

FIGS. 5A-J. SWI/SNF inhibition by mithramycin drives divergent phenotypes in rhabdoid tumor cells. (FIG. 5A) Gene ontology (GO) analysis of genes that were up-regulated by at least 1-log FC in the RNA-seq, ATAC-seq, and H3K27ac ChIP-seq datasets at both 8-hours and 18-hours mithramycin treatment. Venn diagram indicates gene set overlap. 6 of the top 10 pathways up-regulated relate to cell death and apoptosis. (FIG. 5B) IGV tracks of three genes that were up-regulated in the multi-omic analysis described in FIG. 5C. BCL10 and BTG2 play crucial roles in apoptosis while CDKN1A is a cell cycle progression gene. Black bars indicate promoters from hg19 within 2kb of the TSS. (FIG. 5C) FGSEA analysis of the apoptosis hallmark gene set shows enrichment following 8-hours of mithramycin treatment (p-value 4.0e-3). (FIG. 5D) Time course of 100 nM mithramycin exposure in BT12 cells. Cells were treated with 100 nM MMA for the indicated times followed by a replacement of drug-free media. After 8-hours (red) of mithramycin exposures, the cells have an irreversible suppression of proliferation compared to solvent control. (FIG. 5E) Live cell images of BT12 cells treated with 100 nM mithramycin at the indicated times. 100 nM mithramycin leads to cell death, as was described in FIGS. 2A-J. (FIG. 5F) Time course of 20 nM MMA exposure in BT12 cells. Cells were treated with 20 nM MMA for the indicated times followed by a replacement of drug-free media. After 48-hours (red) of mithramycin exposures, the cells no longer proliferate compared to solvent control. (FIG. 5G) Live cell images of BT12 cells treated with 20 nM mithramycin at the indicated times. 20 nM mithramycin treatment leads to lipid accumulation and the appearance of differentiating adipocytes. (FIG. 5H) FGSEA analysis of the stem cell differentiation GO gene set shows enrichment following 8-hours of mithramycin treatment (p-value 3.9e-3). (FIGS. 5I-J) FGSEA analysis of gene ontology terms upregulated in primary AT/RT tumors as described in (Wang et al., 2017) following 8-hours (FIG. 5I) and 18-hours (FIG. 5J) mithramycin treatment. Mithramycin down-regulates all pathways described to be up-regulated in primary AT/RT tumors.

FIGS. 6A-E. Continuous infusion of mithramycin shows activity in an intramuscular rhabdoid tumor xenograft model. (FIG. 6A) Mice with G401 rhabdoid tumor xenografts in the gastrocnemius show no tumor regression when treated with 1 mg/kg bolus injection (3 injections/week for 2-weeks). Treatment duration indicated by gray shaded box. (FIG. 6B) Mice with G401 rhabdoid tumor xenografts in the gastrocnemius exhibit tumor regression with continuous infusion of mithramycin (2.4 mg/kg over 72-hours) compared with vehicle. Treatment duration indicated by gray shaded box. Tumors recurred approximately 12-days after treatment end. (FIG. 6C) Averaged spaghetti plots from FIG. 6A and FIG. 6B with error bars representing standard error. Continuous infusion of mithramycin (purple) prolongs tumor regression compared with bolus injection (teal). Treatment duration indicated by the colored arrows and black dotted lines at treatment completion. (FIGS. 6D-E) Immunohistochemistry analysis of G401 xenograft tumors on 3 days after treatment with vehicle, bolus injections of mithramycin (bolus) (FIG. 6D) or continuous infusion of mithramycin (continuous) (FIG. 6E). 10× magnification of H&E, cleaved caspase 3 as a marker of apoptosis, and H3K27me3 (left to right) of the G401 xenografts. Bolus injection does not increase CC3 or H3K27me3 while continuous infusion significantly increases positive staining of CC3 and H3K27me3. IHC analysis positively correlates tumor response for both mithramycin schedules.

FIGS. 7A-E. EC-8042, a second generation mithramycin analogue, leads to durable tumor regression in vivo. (FIGS. 7A-B) Mice with G401 rhabdoid tumor xenografts in the gastrocnemius exhibit tumor regression with continuous infusion of EC-8042 compared with vehicle. (FIG. 7A) Mice were treated with 30 mg/kg EC-8042 over 72-hours. (FIG. 7B) Mice were treated with 50 mg/kg EC-8042 over 144-hours. Treatment duration indicated by black arrows and gray shaded box. Tumors recurred approximately 40-days after treatment end. (FIG. 7C) Bioluminescence imaging of G401 rhabdoid tumor xenografts correlates with caliper measurements in FIGS. 7A and 7B. Two mice per treatment group were imaged (left) and quantified in the bar graph (right). Error bars represent mean with standard deviation. (FIG. 7D) Tumor measurements for all three treatment groups (vehicle, 3-day pump, 7-day pump) at the start of treatment, end of treatment, and 14-days after the end of the treatment. Both 3-day and 7-day treatment groups exhibit prolonged tumor growth suppression compared to vehicle. (FIG. 7E) Kaplan-Meier survival curves indicating extended survival for both the 3-day pump and 7-day pump treatment cohorts. EC-8042 increases median survival from 28-days in vehicle to 68-days and 70-days in 3-day and 7-day pump cohorts, respectively. Three mice had complete cures in the 3-day pump cohort.

FIGS. 8A-E. EC-8042 induces mesenchymal differentiation and epigenetic reprogramming in vivo. (FIGS. 8A-D) Immunohistochemistry analysis of G401 xenograft tumors on 3 days (left, Day 4) and 7-days (right, Day 8) after treatment with vehicle or 3-day pump of EC-8042. 10× magnification of H3K27me3 (FIG. 8A), H3K27ac (FIG. 8B), human mitochondria (FIG. 8C), and cleaved caspase 3 (FIG. 8D). H3K27me3 and CC3 significantly increase in positive staining by day 4. H3K27ac and human mitochondrial staining decrease by day 4 compared with vehicle. Positive staining of H3K27me3 and CC3 is gone by day 8, as is human mitochondrial staining indicating no residual tumor. (FIG. 8E) Immunohistochemistry analysis of H&E stains from G401 xenograft tumors on 1 day, 3 days, and 7-days after treatment with vehicle, 3-day EC-8042 pump or 7-day EC-8042 pump. EC-8042 treated xenograft tumors exhibit evidence of mesenchymal differentiation compared to vehicle. microCT analysis of xenograft tumors on 7-days after treatment exhibit enhanced calcification compared to vehicle.

(FIGS. 10A-B) Western blot showing concentration-dependent increase in H3K27me3 following exposure to 100 nM, 50 nM, 25 nM mithramycin for 18h in G401 cells (FIG. 10A) but not SMARCB1-complemented G401 cells (FIG. 10B) relative to loading control. (FIGS. 10C-D) Mithramycin evicts BRD9 and SMARCE1 SWI/SNF subunits from chromatin in a time-dependent manner in G401 (FIG. 10C) but not SMARCB1-complemented G401 cells (FIG. 10D) cells. Westner blot analysis showing whole cell lysate (total), cytoplasmic soluble (CS), nuclear soluble (NS), and chromatin bound (Chr) fractions collected after exposure to 100 nM mithramycin for 1 h, 8h or 18 h and probed for the SWI/SNF subunits (BRD9 or SMARCE1) or H3 (chromatin control) and GAPDH (soluble control).

Figure 8E:
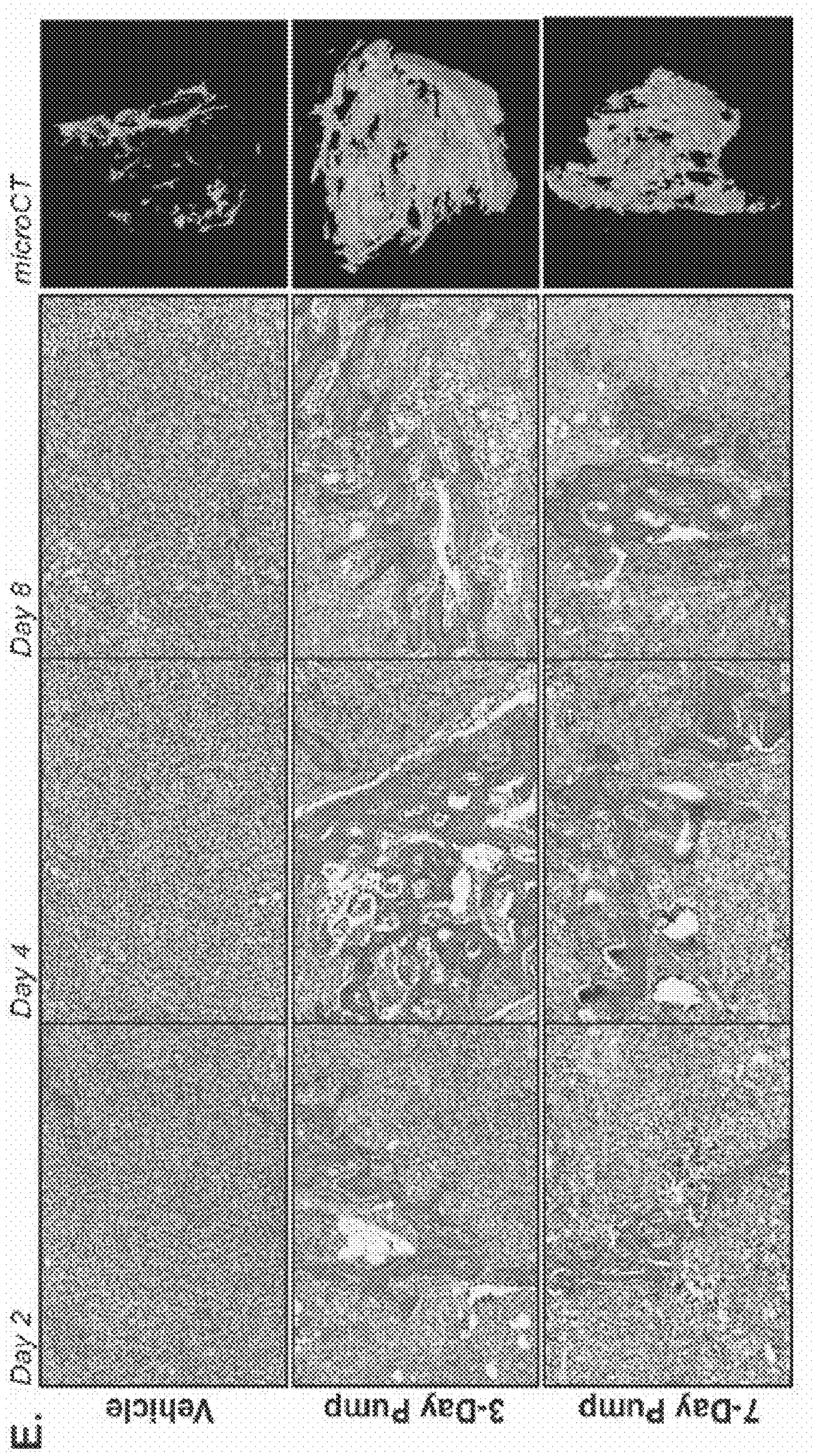
Figure 9:
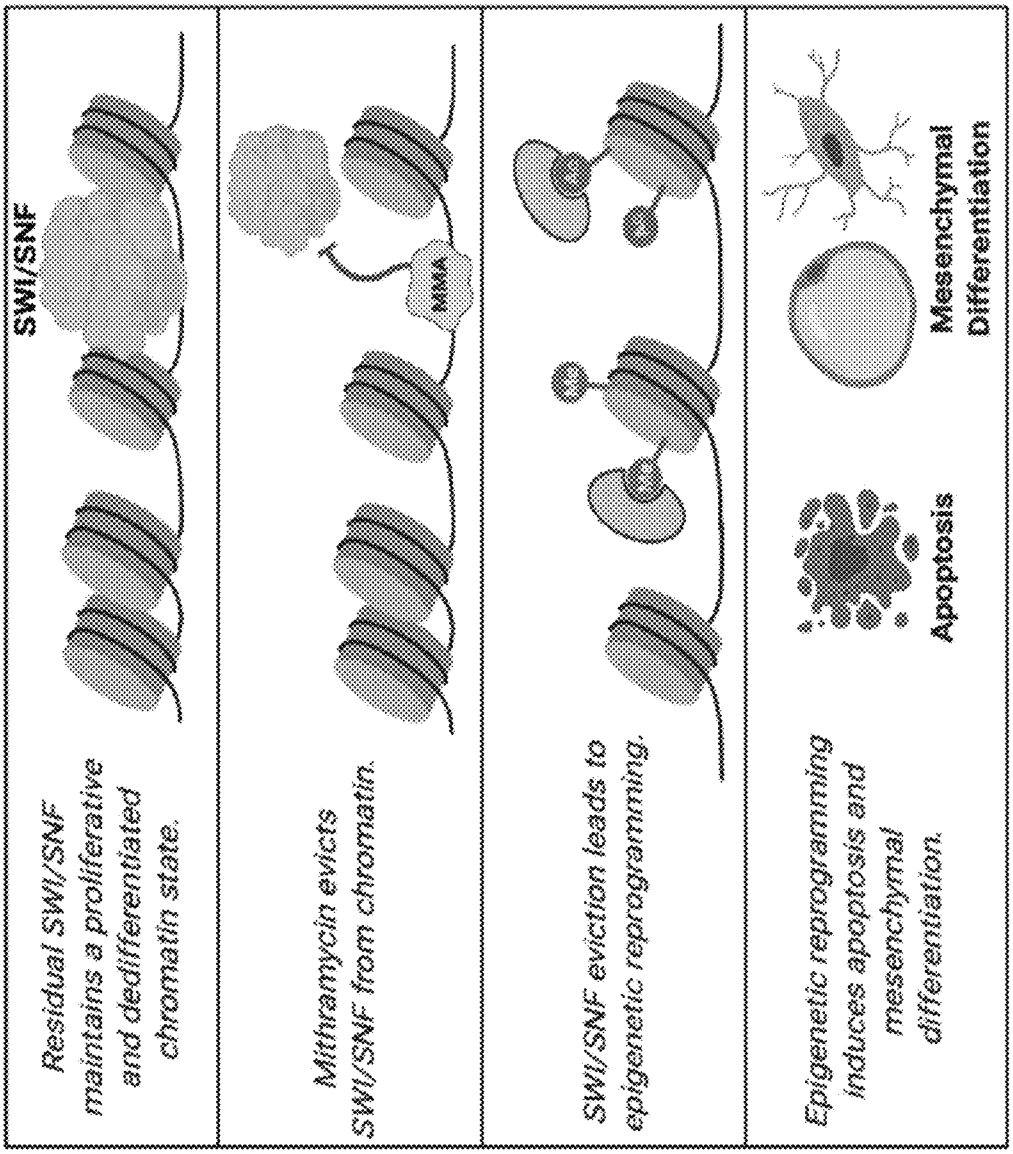
FIG. 9. Schematic of the role SWI/SNP plays in proliferation and de-differentiation and the effect of mithramycin thereon.

FIGS. S1A-E (relating to FIGS. 1A-3H). (FIG. S1A) A pediatric cell line viability screen with mithramycin. Cell lines with mutated or dysregulated SWI/SNF cluster towards the right on the graph indicating these cell lines are more sensitive to mithramycin. Data analyzed from Osgood et al. (2016). (FIG. S1B) Chromatin immunoprecipitation of IgG, SMARCC1 (left), H3K27ac (middle) or H3K27me3 (right) at the control locus, GAPDH. (FIG. S1C) Knockdown of SP1 (black) does not affect BT12 rhabdoid tumor cell proliferation compared with a siNeg (gray, solid line) negative control as measured by live cell imaging in the Incucyte Zoom. siDeath (gray, dotted line) is a positive control for knockdown efficiency. (FIG. S1D) percent input quantification at the control locus GAPDH for IgG, SMARCC1, H3K27ac, and H3K27me3, either with solvent, 8h MMA, or 18h MMA. (FIG. S1E) percent confluency over time for siDeath, siNeg, and siSP1.

FIGS. S2A-C (relating to FIGS. 4A-H). (FIG. S2A) Principal component analysis of ATAC-seq libraries prior to normalization with lambda spike-in controls. Only the first 2 principal components are shown with a scree plot showing all 9 components and variance explained. (FIGS. S2B) Principal component analysis of ATAC-seq libraries post-normalization with lambda spike-in controls using a k of 1 for RUVg. (FIG. S2C) Principal component analysis of ATAC-seq libraries post-normalization with lambda spike-in controls using a k of 4 for RUVg. Notably, treatment level clusters are lost using the spike-ins as control "genes" within the first 4 factors, suggesting that library complexity can be accounted for or confounding if not addressed as dominant sources of variation in the data.

FIGS. S3A-H (relating to FIGS. 4A-H). (FIG. S3A) Profile traces that correspond with the heatmaps plotted in FIG. 4C for regions that increase in H3K27ac (red) and regions that decrease in H3K27ac (blue) from solvent to 8-hours (top) and 18-hours (bottom) mithramycin treatment. (FIG. S3B) Profile traces that correspond with the heatmaps plotted in FIG. 4C for regions that increase in accessibility (red) and regions that decrease in accessibility (blue) from solvent to 8-hours (top) and 18-hours (bottom) mithramycin treatment. (FIGS. S3C-E) Heatmaps and profile tracing showing H3K27ac ChIP-seq peaks following mithramycin treatment for all three experimental replicates. A 2kb window is centered on the TSS. (FIGS. S3F-H) Heatmaps and profile tracing showing ATAC-seq peaks following mithramycin treatment for all three experimental replicates. A 2kb window is centered on the TSS.

FIGS. S4A-D (relating to FIGS. 4A-5J). (FIGS. S4A-B) RNA-seq reactome pathway analysis of the genes down-regulated after 8-hours (FIG. S4A) and up-regulated after 18-hours (FIG. S4B) Mithramycin treatment. (FIG. S4C) Venn diagram of overlapping gene sets with at least a 1 log FC decrease in both 8-hours and 18-hours mithramycin treatment compared with solvent. 25 genes were down-regulated at both time points for RNA-seq, ATAC-seq, and H3K27ac ChIP-seq. (FIG. S4D) Time course of 100 nM mithramycin exposure in G401 rhabdoid tumor cells. Cells were treated with 100 nM MMA for the indicated times followed by a replacement of drug-free media. After 8-hours (red) of mithramycin exposures, the cells have an irreversible suppression of proliferation compared to solvent control.

FIGS. S5A-C (relating to FIGS. 7A-E). (FIG. S5A) Dose response curve of BT12 (circle) and G401 (triangle) rhabdoid tumor cells treated with EC-8042. Both rhabdoid tumor cell lines are sensitive to EC-8042. (FIG. S5B) Incucyte zoom live cell images in BT12 rhabdoid tumor cells treated with mithramycin and EC-8042. EC-8042 (200 nM) leads to lipid accumulation and a flattened cell phenotype compared with mithramycin (100 nM). (FIG. S5C) Mice treated with EC-8042 have reversible body mass loss during treatment with the 3-day pump (middle) and the 7-day pump (right) compared to vehicle (left). However, body weight recovers once treatment ends.

FIGS. S6A-B (relating to FIGS. 8A-E). (FIG. S6A) Immunohistochemistry analysis of G401 xenograft tumors on 3 days (left, Day 4) and 7-days (right, Day 8) after treatment with vehicle or 7-day pump of EC-8042. 10× magnification of H3K27me3, H3K27ac, human mitochondria, cleaved caspase 3, and Ki67 correlate with vehicle and 3-day EC-8042 pump in FIGS. 8A-E. (FIG. S6B) Immunohistochemistry analysis of G401 xenograft tumors on 3 days (left, Day 4) and 7-days (right, Day 8) after treatment with vehicle or 3-day pump of EC-8042. 10× magnification of Ki67 correlates with the IHC shown in FIGS. 8A-E.

DESCRIPTION OF ILLUSTRATIVE EMBODIMENTS

In this study, the inventors will show that the small molecule mithramycin and its second-generation analogue EC-8042 inhibit residual SWI/SNF activity. They previously identified mithramycin as an important therapeutic agent in Ewing sarcoma (Grohar et al., 2011). As part of these studies, they found that rhabdoid tumor was extremely sensitive to the drug (Osgood et al., 2016). Due to the relationship of both tumors to SWI/SNF and the dependence of rhabdoid tumor on this complex, the inventors hypothesized mithramycin disrupts SWI/SNF activity (Boulay et al., 2017). Indeed, mithramycin evicts SWI/SNF from chromatin to induce epigenetic reprogramming, chromatin compartment remodeling and reversal of the oncogenic phenotype. This reprogramming leads to apoptosis and at the same time re-establishes the differentiation program leading to differentiation of rhabdoid tumor xenografts into benign mesenchymal tissue. Together, these results define a mithramycin based therapy as a clinical candidate for rhabdoid tumor.

These and other aspects of the disclosure are described in greater detail below.

I. SWI/SNF

In molecular biology, SWI/SNF (SWItch/Sucrose Non-Fermentable),[1] is a nucleosome remodeling complex found in eukaryotes. In simpler terms, it is a group of proteins that associate to remodel the way DNA is packaged. It is composed of several proteins—products of the SWI and SNF genes (SWI1, SWI2/SNF2, SWI3, SWI5, SWI6) as well as other polypeptides. It possesses a DNA-stimulated ATPase activity and can destabilise histone-DNA interactions in reconstituted nucleosomes in an ATP-dependent manner, though the exact nature of this structural change is unknown.

The human analogues of SWI/SNF are BAF (SWI/SNF-A) and PBAF (SWI/SNF-B). BAF in turn stands for "BRG1- or HBRM-associated factors" and PBAF is for "polybromo-associated BAF."

It has been found that the SWI/SNF complex (in yeast) is capable of altering the position of nucleosomes along DNA. Two mechanisms for nucleosome remodeling by SWI/SNF have been proposed. The first model contends that a unidirectional diffusion of a twist defect within the nucleosomal DNA results in a corkscrew-like propagation of DNA over the octamer surface that initiates at the DNA entry site of the nucleosome. The other is known as the "bulge" or "loop-recapture" mechanism and it involves the dissociation of DNA at the edge of the nucleosome with reassociation of DNA inside the nucleosome, forming a DNA bulge on the octamer surface. The DNA loop would then propagate across the surface of the histone octamer in a wave-like manner, resulting in the repositioning of DNA without changes in the total number of histone-DNA contacts. A recent study has provided strong evidence against the twist diffusion mechanism and has further strengthened the loop-recapture model.

The mammalian SWI/SNF (mSWI/SNF) complex functions as a tumor suppressor in many human malignancies. Early studies identified that SWI/SNF subunits were frequently absent in cancer cell lines. It was first identified in 1998 as a tumor suppressor in rhabdoid tumors, a rare pediatric malignancy. As DNA sequencing costs diminished, many tumors were sequenced for the first time around 2010. Several of these studies revealed SWI/SNF to be a tumor suppressor in a number of diverse malignancies. Several studies revealed that subunits of the mammalian complex, including SMARCB1, PBRM1, SMARCB1, SMARCA4, and ARID2, are frequently mutated in human cancers. A meta-analysis of many sequencing studies demonstrated SWI/SNF to be mutated in approximately 20% of human malignancies.

SMARCB1 has been shown to interact with SMARCB1, BAZ1B, BRCA1, CREB-binding protein, Cyclin-dependent kinase 8, Myc, P53, POLR2A, PPP1CA, PPP1CB, PPP1CC, PPP1R15A, SMARCA2, SMARCA4, SMARCC1, SMARCE1, SS18, and XPO1. It is associated with the development of rhabdoid tumors (see below).

An exemplary protein accession number for human SMARCB1 is NP_001007469 (SEQ ID NO: 1). An exemplary mRNA accession number for human SMARCB1 is NM_001007468 (SEQ ID NO: 2).

III. EC-8042

EC-8042 (demycarosyl-3D-β-D-ditioxosyl-mithramycin SK (DIG-MSK) is a mithramycin analogue proposed for the treatment of cancer cells having mutated/deficient/defect SMARCB1. The structure of EC-8042 is shown below:

EC-8042

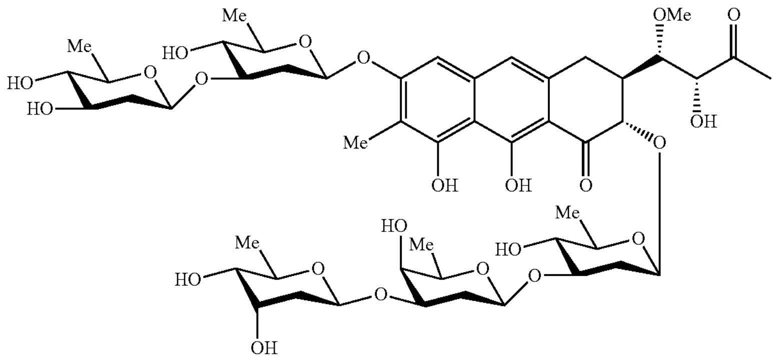

Electron microscopy studies of SWI/SNF and RSC (SWI/SNF-B) reveal large, lobed 1.1-1.3 MDa structures. No atomic-resolution structures of the entire SWI/SNF complex have been obtained to date, due to the protein complex being highly dynamic and composed of many subunits. However, domains and several individual subunits from yeast and mammals have been described. In particular, the cryo-EM structure of the ATPase Snf2 in complex with a nucleosome shows that nucleosomal DNA is locally deformed at the site of binding. A model of the mammalian ATPase SMARCA4 shows similar features, based on the high degree of sequence homology with yeast Snf2. The interface between two subunits, BAF155 (SMARCC1) and BAF47 (SMARCB1) was also resolved, providing important insights into the mechanisms of the SWI/SNF complex assembly pathway.

II. SMARCB1

SWI/SNF-related matrix-associated actin-dependent regulator of chromatin subfamily B member 1 is a protein that in humans is encoded by the SMARCB1 gene. The protein encoded by this gene is part of a complex that relieves repressive chromatin structures, allowing the transcriptional machinery to access its targets more effectively. The encoded nuclear protein may also bind to and enhance the DNA joining activity of HIV-1 integrase. This gene has been found to be a tumor suppressor, and mutations in it have been associated with malignant rhabdoid tumors. Two transcript variants encoding different isoforms have been found for this gene.

It has been shown to be activate against triple-negative breast cancers and Ewing sarcoma. It is in pre-clincal development by Entrechem.

IV. Treating Cancers

A. Cancers

Cancer encompasses a group of diseases involving abnormal cell growth with the potential to invade or spread to other parts of the body. These contrast with benign tumors, which do not spread to other parts of the body. Possible signs and symptoms include a lump, abnormal bleeding, prolonged cough, unexplained weight loss and a change in bowel movements. While these symptoms may indicate cancer, they may have other causes. Over 100 types of cancers affect humans.

Cancer can spread from its original site by local spread, lymphatic spread to regional lymph nodes or by hematogenous spread via the blood to distant sites, known as metastasis. When cancer spreads by a hematogenous route, it usually spreads all over the body. The symptoms of metastatic cancers depend on the tumor location and can include enlarged lymph nodes (which can be felt or sometimes seen under the skin and are typically hard), enlarged liver or enlarged spleen, which can be felt in the abdomen, pain or fracture of affected bones and neurological symptoms.

Many treatment options for cancer exist. The primary ones include surgery, chemotherapy, radiation therapy, hormonal therapy, targeted therapy and palliative care. Which treatments are used depends on the type, location and grade of the cancer as well as the patient's health and personal wishes. The treatment intent may or may not be curative.

The therapeutic methods of the disclosure in general include administration of a therapeutically effective amount of compositions described herein to a subject in need thereof, including a mammal, particularly a human. Such treatment will be suitably administered to subjects, particularly humans, suffering from cancer or having a symptom thereof.

Cancers may be a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. More specifically, the tumors will have a mutation in the SWI-SNF pathway. In a particular embodiment, the cancer may be a rhabdoid cancer, such as malignant rhabdoid tumor, atypical teratoid rhabdoid tumor or rhabdoid tumor of the kidney.

Malignant rhabdoid tumor (MRT) is a very aggressive form of tumor originally described as a variant of Wilms' tumor, which is primarily a kidney tumor that occurs mainly in children. MRT was first described as a variant of Wilms' tumor of the kidney in 1978. MRTs are a rare and highly malignant childhood neoplasm. Rhabdoid tumors outside the kidney were later reported in many tissues including the liver, soft tissue, and the central nervous system. Several cases of primary intracranial MRT have been reported since its recognition as a separate entity in 1978. The term rhabdoid was used due to its similarity with rhabdomyosarcoma under the light microscope. The exact pathogenesis of MRT is unknown.

The cerebellum is the most common location for primary intracerebral MRT (i.e., atypical teratoid rhabdoid tumor). Although the cell of origin is not known, cytogenetic studies have suggested a common genetic basis for rhabdoid tumors regardless of location with abnormalities in chromosome 22 commonly occurring.

There have been reported cases of a child having both atypical teratoid rhabdoid tumors in the brain as well as rhabdoid tumors of the kidney. Weeks and associates reported on 111 renal rhabdoid cases of which 13.5% also had a central nervous system malignancy. It has been hypothesized that a germline INI mutation may predispose a child to these tumors. There have been some references in the literature alluding to a new diagnosis called rhabdoid predisposition syndrome related to the gene hSNF5/INI1.

Considerable debate has been focused on whether atypical teratoid rhabdoid tumors are the same as rhabdoid tumors of the kidney (i.e., just extrarenal MRTs). The recent recognition that both CNS atypical teratoid/rhabdoid tumors and MRTs have deletions of the INI1 gene in chromosome 22 indicates that rhabdoid tumors of the kidney and brain are identical or closely related entities, although the CNS variant tends to have its mutations on Taxon 9 and MRTs elsewhere. This observation is not surprising because rhabdoid tumors at both locations possess similar histologic, clinical, and demographic features. Moreover, 10-15% of patients with MRTs have synchronous or metachronous brain tumors, many of which are second primary malignant rhabdoid tumors. This similarity excludes composite rhabdoid tumors, which occur mainly in adults.

The histologic diagnosis of malignant rhabdoid tumor depends on identification of characteristic rhabdoid cells—large cells with eccentrically located nuclei and abundant, eosinophilic cytoplasm. However, the histology can be heterogeneous and the diagnosis of MRT can often be difficult. Misclassifications can occur.

In MRTs, the INI1 gene (SMARCB1) on chromosome 22q functions as a classic tumor suppressor gene. Inactivation of INI1 can occur via deletion, mutation, or acquired UPD.

In a recent study, Single nucleotide polymorphism array karyotyping identified deletions or LOH of 22q in 49/51 rhabdoid tumors. Of these, 14 were copy neutral LOH (or acquired UPD), which is detectable by SNP array karyotyping, but not by FISH, cytogenetics, or array CGH. MLPA detected a single exon homozygous deletion in one sample that was below the resolution of the SNP array. SNP array karyotyping can be used to distinguish, for example, a medulloblastoma with an isochromosome 17q from a primary rhabdoid tumor with loss of 22q11.2. When indicated, molecular analysis of INI1 using MLPA and direct sequencing may then be employed. Once the tumor-associated changes are found, an analysis of germline DNA from the patient and the parents can be done to rule out an inherited or de novo germline mutation or deletion of INI1, so that appropriate recurrence risk assessments can be made.

Regardless of location, all rhabdoid tumors are highly aggressive, have a poor prognosis, and tend to occur in children less than two years of age.

B. Theranostic Methods

In one embodiment, the disclosure provides methods to assess the SMARCB1 status of a cancer being treated. The method includes the step of determining whether a cancer patient's cancer has a mutated SMARCB1 gene or protein prior to administering a therapeutic composition as described herein. The analysis is useful in predicting whether the subject will respond to a glutamate metabolism inhibitor—if so, then the glutamate inhibitor is administered, and if not, then another therapy is employed. The following exemplary techniques can be employed to examine SMARCB1 status.

1. Nucleic Acid-Based Detection Methods

Nucleic acid-based detection methods may be employed to identify cancers with mutant SMARCB1. The following is a discussion of such methods, which are applicable to assessing mutations in SMARCB1. In certain embodiments, the disclosure relates to methods of characterizing and treating cancer by detecting mutant SMARCB1. The methods of the disclosure can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

i. Hybridization

Methods looking at DNA or mRNA all fundamentally rely, at a basic level, on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Molecules having complementary sequences over contiguous stretches greater than 20 bases in length are generally preferred, to increase stability and selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

ii. Nucleic Acid Amplification

Since many mRNAs are present in relatively low abundance, nucleic acid amplification greatly enhances the ability to assess expression. The general concept is that nucleic acids can be amplified using paired primers flanking the region of interest. The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to selected genes are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best-known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641.

Polymerase chain reaction methodologies are well known in the art. Representative methods of RT-PCR are described in U.S. Pat. No. 5,882,864.

Whereas standard PCR usually uses one pair of primers to amplify a specific sequence, multiplex-PCR (MPCR) uses multiple pairs of primers to amplify many sequences simultaneously. The presence of many PCR primers in a single tube could cause many problems, such as the increased formation of misprimed PCR products and "primer dimers," the amplification discrimination of longer DNA fragment and so on. Normally, MPCR buffers contain a Taq Polymerase additive, which decreases the competition among amplicons and the amplification discrimination of longer DNA fragment during MPCR. MPCR products can further be hybridized with gene-specific probe for verification. Theoretically, one should be able to use as many as primers as necessary. However, due to side effects (primer dimers, misprimed PCR products, etc.) caused during MPCR, there is a limit (less than 20) to the number of primers that can be used in a MPCR reaction. See also European Application No. 0 364 255 and Mueller and Wold (1989).

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence-based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

iii. Detection of Nucleic Acids

Following any amplification, it may be desirable to separate the amplification product from the template and/or the excess primer. In one embodiment, amplification products are separated by agarose, ag arose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be achieved by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

iv. Nucleic Acid Arrays

Microarrays comprise a plurality of polymeric molecules spatially distributed over, and stably associated with, the surface of a substantially planar substrate, e.g., biochips. Microarrays of polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e., target, such as polyA mRNA from a particular tissue type. Contact is carried out under hybridization conditions and unbound nucleic acid is then removed. The resultant pattern of hybridized nucleic acid provides information regarding the genetic profile of the sample tested. Methodologies of gene expression analysis on microarrays are capable of providing both qualitative and quantitative information.

A variety of different arrays which may be used are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single- or double-stranded, usually single-stranded, and may be PCR fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA.

A variety of different endonucleases are known and may be used, where such nucleases include: mung bean nuclease, S1 nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3' end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

2. Protein-Based Detection Methods i. Immunodetection

In still further embodiments, there are immunodetection methods for identifying and/or quantifying mutant SMARCB1. These methods may, in certain embodiments, be applied to the treatment of cancer, such as those discussed above.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of TSP1 antibodies also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to SMARCB1 present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

ii. ELISAs

Immunoassays, in their most simple sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the TSP1 is added to the wells. After binding and washing to remove non-specifically bound immune complexes, the bound antigen may be detected. Detection may be achieved by the addition of another anti-SMARCB1 antibody that is linked to a detectable label. This type of ELISA is a simple "sandwich ELISA." Detection may also be achieved by the addition of a second anti-SMARCB1 antibody, followed by the addition of a third antibody that has binding affinity for the second antibody, with the third antibody being linked to a detectable label.

In another exemplary ELISA, the samples suspected of containing the SMARCB1 are immobilized onto the well surface and then contacted with anti-SMARCB1 antibody. After binding and washing to remove non-specifically bound immune complexes, the bound anti-SMARCB1 antibodies are detected. Where the initial anti-SMARCB1 antibodies are linked to a detectable label, the immune complexes may be detected directly. Again, the immune complexes may be detected using a second antibody that has binding affinity for the first anti-SMARCB1 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

iii. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

iv. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

v. Immunodetection Kits

In still further embodiments, there are immunodetection kits for use with the immunodetection methods described above. The immunodetection kits will thus comprise, in suitable container means, a first antibody that binds to TSP1 antigen, and optionally an immunodetection reagent.

In certain embodiments, the TSP1 antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with embodiments discussed herein.

The kits may further comprise a suitably aliquoted composition of the TSP1 antigen, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits will also include a means for containing the antibody, antigen, and any other reagent containers in close confinement for commercial sale. Such containers may include injection or blow-molded plastic containers into which the desired vials are retained.

VI. Mass Spectrometry

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) while newer quantitative methods are being developed using matrix assisted laser desorption/ionization (MALDI) followed by time of flight (TOF) MS. In particular, mass spectrometry has been applied to samples to identify proteins targets therein.

ESI is a convenient ionization technique that is used to produce gaseous ions from highly polar, mostly nonvolatile biomolecules, including lipids. The sample is injected as a liquid at low flow rates (1-10 μL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals and bioactive peptides. Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide. Protein quantification has been achieved by quantifying tryptic peptides. Complex mixtures such as crude extracts can be analyzed, but in some cases sample clean up is required.

Secondary ion mass spectroscopy, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments is due to different size causing different velocity. Each ion mass will thus have a different flight-time to the detector.

One can either form positive ions or negative ions for analysis. Positive ions are made from regular direct photoionization, but negative ion formation requires a higher-powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectrum.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

Since its inception and commercial availability, the versatility of MALDI-TOF-MS has been demonstrated convincingly by its extensive use for qualitative analysis. For example, MALDI-TOF-MS has been employed for the characterization of synthetic polymers, peptide and protein analysis, DNA oligonucleotide sequencing, and the characterization of recombinant proteins. Recently, applications of MALDI-TOF-MS have been extended to include the direct analysis of biological tissues and single cell organisms with the aim of characterizing endogenous peptide and protein constituents.

The properties that make MALDI-TOF-MS a popular qualitative tool-its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use. These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products, whereas other studies have demonstrated the potential of MALDI-TOF-MS for the quantification of biologically relevant analytes such as neuropeptides, proteins, antibiotics, or various metabolites in biological tissue or fluid. In earlier work, it was shown that linear calibration curves could be generated by MALDI-TOF-MS provided that an appropriate internal standard was employed. This standard can "correct" for both sample-to-sample and shot-to-shot variability. Stable isotope labeled internal standards (isotopomers) give the best result.

With the marked improvement in resolution available on modern commercial instruments, primarily because of delayed extraction, the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated but are not used routinely.

C. Combination Therapies

It may also be useful to treat cancers using the methods and compositions of the present disclosure, but further employ at least one other therapy. The present therapy and the other therapy would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the antibody may precede or follow the other treatment by intervals ranging from minutes to weeks. One would generally ensure that a significant period of time did not expire between each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired.

Various combinations may be employed, where the glutamate metabolism inhibitor of the present disclosure is "A," and the other therapy is "B," as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | | B/A/B/A | B/A/A/B | B/B/B/A |
| A/A/A/B | B/A/A/A | A/B/A/A | A/A/B/A | | A/B/B/B | B/A/B/B | B/B/A/B |

Some agents or therapies suitable for use in a combined therapy with agents according to the present disclosure against cancer are discussed below, although other combinations are contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBT-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammalI and calicheamicin omegaI1; dynemicin, including dynemicin A uncialamycin and derivatives thereof; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein transferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8, and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311).

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believed to be particularly efficacious in reducing the reoccurrence of the tumor. Additionally, the compounds of the present disclosure can also be used in a neoadjuvant setting.

It also should be pointed out that any of the foregoing therapies may prove useful by themselves in treating cancer.

V. Examples

The following examples are included to demonstrate preferred embodiments. It should be appreciated by those of skill in the art that the techniques disclosed in the examples which follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods

Cell Culture. BT12 and CHLA266 cell lines were obtained from the Children's Oncology Group. G401 cell line was obtained from ATCC. TC32 cells were obtained from Dr. Lee Helman (Children's Hospital of Los Angeles). U2OS cells were obtained from Dr. Chand Khanna (Ethos Veterinary Health LLC). All cell lines were grown in RPMI-1640 medium (Invitrogen) supplemented with 10% fetal bovine serum (Gemini Bio-Products), 2 mM L-glutamine (Invitrogen), 100 U/mL penicillin and 100 μg/mL streptomycin (Invitrogen). Cell lines were maintained at less than 80% confluency at 37° C. and 5% $CO_2$ and confirmed to be *mycoplasma* negative every 6-months.

Quantitative real-time PCR (RT-qPCR). 250,000 BT12, CHLA266, or G401 were incubated with mithramycin in 6-well plates. RNA was subsequently collected using the RNeasy kit and quantified. The RNA was reverse transcribed with the high capacity reverse transcriptase kit (Life Technologies) at 25° C. for 10 minutes, 37° C. for 120 minutes, and 85° C. for 5 minutes. 100 ng cDNA was PCR amplified with 2×SYBR green at 95° C. for 10 min, 95° C. for 15 s, 55° C. for 15s, and 72° C. for 1 min, for 40 cycles. Expression from three independent experiments performed in duplicate was calculated with standard ddCT methods relative to GAPDH and solvent controls.

Cell Proliferation Assays. $IC_{50}$s were calculated with non-linear regression (Graphpad Prism) as the average of three independent experiments performed in duplicate. Cell viability was measured using MTS assay CellTiter96 (Promega) plotted against a standard curve and was confirmed with real-time proliferation assays on the Incucyte Zoom, as previously described (Harlow et al., 2019).

Western Blot. 2.5 million BT12 cells were incubated with mithramycin in 10 $cm^2$ plates, washed and collected in PBS. Whole cell lysates were lysed with 4% lithium dodecyl sulfate (LDS) lysis buffer. Cellular fractionation was performed to separate cytoplasmic and nuclear fractions. Fractionation lysates were lysed with cytoplasmic lysis buffer (25 mM HEPES pH 8.0, 50 mM KCl, and 05% NP-40) supplemented with RNAse (Thermo Fisher Scientific) and protease inhibitors (Sigma-Aldrich) for 15-minutes on ice vortexing every 5-minutes. The nuclei were pelleted at 1500× g for 5 minutes and the cytoplasmic fraction was isolated. The nuclei pellet was lysed with 4% LDS lysis buffer. Following dilution of detergent, protein was quantified with the BCA colorimetric assay (Thermo-Scientific). 30 μg of protein were separated on NuPage 4-12% Bis-Tris in 1× NuPage MOPS SDS buffer and transferred to a nitrocellulose membrane in 1× Tris-Glycine-SDS buffer with 20% methanol. Transfer was run at 20 V and 4° C. overnight. The membranes were blocked with 5% milk in TBS-T (1×TBS, 0.1% Tween-20) and probed with Abcam (H3K27me3), EMD Millipore (SP1), and Cell Signaling (SMARCC1, SMARCE1, H3) antibodies.

Chromatin Fractionation. 3 million BT12, G401, or U20S were incubated with 100 nM mithramycin or PBS control for 8 or 18-hours. Cells were washed and collected in PBS, incubated in CSK buffer (100 mM NaCl, 300 mM sucrose, 3 mM $MgCl_2$, 0.1% Triton X-100, 10 nM PIPES (pH 7.0), Roche Complete EDTA-free protease inhibitor) for 20 minutes on ice. The total fraction was collected. The soluble fraction was collected by centrifugation at 1,300× g for 5 minutes at 4° C. The insoluble nuclear pellet was washed in CSK and centrifugated at 1,3000×g for 5 minutes at 4° C. The chromatin pellet was resuspended with CSK buffer supplemented with nuclease (Pierce Universal Nuclease), incubated for 20 minutes on ice, then the chromatin fraction was collected by centrifugation at 1,300×g for 5 minutes at 4° C. Total protein was quantitated by Bradford assay (Bio-Rad Protein Assay Dye Reagent Concentrate). Chromatin protein and soluble protein quantitation was calculated from the total protein quantitation. 10 g of each protein sample were resolved as describe above (see: Western Blot).

RNA-Sequencing. RNA was extracted from three biological replicates for each experimental time point, as described above. RNA was submitted for 1×75 bp sequencing. Libraries were prepared by the Van Andel Genomics Core from 500 ng of total RNA using the KAPA stranded mRNAseq Kit (v5.17) (Kapa Biosystems, Wilmington, MA USA). RNA was sheared to 300-400 bp. Prior to PCR amplification, cDNA fragments were ligated to Bioo Scientific NEXTflex dual adapters (Bioo Scientific, Austin, TX, USA). Quality and quantity of the finished libraries were assessed using a combination of Agilent DNA High Sensitivity chip (Agilent Technologies, Inc.), QuantiFluor® dsDNA System (Promega Corp., Madison, WI, USA), and Kapa Illumina Library Quantification qPCR assays (Kapa Biosystems). Individually indexed libraries were pooled and 75 bp, single read sequencing was performed on an Illumina NextSeq 500 sequencer using a 75 bp HO sequencing kit (v2) (Illumina Inc., San Diego, CA, USA). Base calling was done by Illumina NextSeq Control Software (NCS) v2.0 and output of NCS was demultiplexed and converted to FastQ format with Illumina Bcl2fastq v1.9.0.

Reads were aligned to hg19 (chromosomes 1-22, X and rCRS) using STAR (v2.7.0f) (Dobin et al., 2013). The index was prepared using default parameters except for --sjdbOverhang 75 and --sjdbGTFfile, where the Gencode v19 annotations were used. Default parameters were used for alignment with the following modifications: --readFiles-Command zcat --outReadsUnmapped None --quantMode GeneCounts --outSAMtype BAM SortedByCoordinate. Alignment rates were between 86-92% across samples. Gene-level transcript quantification was performed using STAR's built-in quantification algorithm as noted in the modified alignment parameters. Genes considered for differential expression analysis were restricted to known, protein-coding genes and lincRNAs present in the Gencode v19 annotations. Libraries were normalized using trimmed mean of M-values (TMM) after filtering for low abundance transcripts using the R (v3.6.1) package edgeR (Robinson, McCarthy, & Smyth, 2010; Robinson & Oshlack, 2010). Briefly, transcripts were retained if they had greater than 1 count per million (CPM) in at least three samples. Transcripts per million (TPM) tables were generated by first computing read per-kilobase mapped (RPKM) and then converting to TPM. Differential expression analysis was carried out using limma-voom (v3.40.6), testing for mithramycin treatment differences (Law, Chen, Shi, & Smyth, 2014; Ritchie et al., 2015). Statistically significant genes were determined using a cutoff of $q<0.05$ and further refined for downstream analyses. Heatmaps were generated using the pheatmap (v1.0.12) package in R. Gene set enrichment analysis was performed with functional gsea (v1.10.1) package in R with 1000 permutations per geneset (Sergushichev, 2016). Reactome pathway analysis was performed with the differential expression analysis analyzed by the reactomePA (v1.28.0) package in R (Yu & He, 2016).

Primary explant normal skull osteoblast raw RNA-seq data was downloaded from the SRA study SRP038863 (Rojas-Pena et al., 2014). Data were aligned and preprocessed as described above. Principal component analysis was carried out using log 2(TPM+1) counts and the prcomp function from the stats package (v3.6.1) in R. Results were plotted using ggplot2 (v3.2.1) and the *viridis* (v0.5.1) packages.

Chromatin Immunoprecipitation (ChIP). 12 million BT12 cells were incubated with 100 nM mithramycin for 8-hours or 18-hours in 15 $cm^2$ plates. Solvent controls were incubated with PBS for 18-hours. BT12 cells were washed with RPMI-1640 media and equilibrated to room temperature. Cross-linking was performed with 16% methanol-free formaldehyde for 4 minutes and quenched for 5 minutes with 0.2 M glycine. Cells were scraped in cold PBS with 1× protease inhibitor (Sigma Aldrich). Cells were lysed in 20 mM Tri-HCl (pH 7.5), 85 mM KCl, and 0.5% NP-40 for 15 minutes on ice and nuclei were released with dounce homogenizing. Chromatin was sheared with Covaris E220 evolution focused sonicator (Covaris) for 8 minutes. 10 μg solubilized chromatin was immunoprecipitated with 1 μg mouse IgG (Abcam) and 1 μg H3K27me3 (Abcam); 2 μg rabbit IgG (Cell Signaling) and 2 μg SMARCC1 (Cell Signaling); 1 μg rabbit IgG (Cell Signaling) and 1 μg H3K27ac (Active Motif) or Antibody-chromatin complexes were pulled down with *Magna* ChIP protein A+G magnetic beads (EMD Millipore) and washed. ChIP DNA was eluted with 100 mM $NaHCO_3$, 1% SDS, and 1× proteinase K for 2-hours at 65° C. followed by 10-minute incubation at 95° C. ChIP DNA was purified with QiaQuick purification kit (Qiagen). Pull down was confirmed with quantitative PCR (see below). Purified ChIP DNA was submitted for 2×75 bp sequencing.

Chromatin Immunoprecipitation with quantitative PCR (ChIP-qPCR). ChIP DNA was quantified with SYBR green relative to a standard curve generated with chromatin from the respective sample for each primer set. qPCR as described above was performed with the following primer sets (GAPDH, MYT1, SOX2, CCND1, SP1).

Chromatin immunoprecipitation with high throughput sequencing (ChIP-seq). Libraries for Input and IP samples were prepared by the Van Andel Genomics Core from 10 ng of input material and either 10ng or all available IP material using the KAPA Hyper Prep Kit (v6.17) (Kapa Biosystems, Wilmington, MA USA). Prior to PCR amplification, end-repaired and A-tailed DNA fragments were ligated to Bioo Scientific NEXTflex Adapters (Bioo Scientific, Austin, TX, USA). Quality and quantity of the finished libraries were assessed using a combination of Agilent DNA High Sensitivity chip (Agilent Technologies, Inc.), QuantiFluor® dsDNA System (Promega Corp., Madison, WI, USA), and Kapa Illumina Library Quantification qPCR assays (Kapa Biosystems). 50 bp, paired end sequencing was performed on an Illumina NovaSeq sequencer using an S2 100 bp sequencing kit (Illumina Inc., San Diego, CA, USA). Base calling was done by Illumina RTA v3.0 software and output of RTA was demultiplexed and converted to FastQ format with Illumina Bcl2fastq2 v2.20.0.

Reads were aligned using bwa mem, duplicate marked with samblaster, and filtered and converted to BAM format using samtools (Faust & Hall, 2014; Li et al., 2009). Aligned reads were retained if they were aligned and had a minimum mapping quality of 20 (e.g. –F 4-q 20 flags in samtools). BAMs were ingested into R (v3.6.1) and processed using csaw (v1.18.0). Briefly, a 150 bp sliding window with a 50 bp step-size was used to summarize the read counts with a maximum fragment size set to 800 bp (Lun & Smyth, 2014, 2016). Next, the background was estimated using a 5kb sliding window where reads were binned and summarized. Regions were excluded if they overlapped known blacklist regions in hg19 (Amemiya, Kundaje, & Boyle, 2019). Regions having signal greater than log 2(3) fold-change over background were retained for differential binding analysis. The first principal component was regressed out of the data due to a batch effect being present prior to downstream analysis. Differential binding analysis was carried out using csaw and edgeR, fitting a quasi-likelihood (QL) negative binomial generalized log-linear model that estimates the prior QL dispersion distribution robustly. Differences were tested using an anova-like test or individual contrasts to generate initial differentially bound regions (DBR). Windows were merged with a maximum width of 5kb and a tolerance of 100 bp between adjacent windows to consider being combined. Next, p-values were combined across clustered sites using Simes' method to control the cluster false discovery rate as implemented in the combineTests function in csaw. Finally, clustered DBRs were defined as having a $q<0.05$.

Assay for Transposase Accessible Chromatin with High Throughput Sequencing (ATAC-seq). 1.5 million BT12 cells were treated with 100 nM mithramycin or PBS control for 8-hours or 18-hours. PBS control was treated for 18-hours. Cells were washed and collected in cold PBS. 25,000 viable BT12 cells were used to perform omni-ATAC with minor modifications (Corces et al., 2017). Prior to transposition, 0.1 ng lambda phage (Thermo Fisher Scientific) was added to the BT12 nuclei pellet. Transposition was carried out for 60-minutes at 37° C. with 1000 rpm mixing. After purification, 0.1 ng phiX DNA were added to the transposition DNA prior library amplification. Libraries were amplified and purified as described. Libraries were purified with the Zymo DNA Clean & Concentrator kit.

Finished libraries were size-selected to retain fragments between 200-800 bp using double sided SPRI selection with Kapa Pure Beads (Kapa Biosbaseystems, Wilmington, MA USA). Right sided selection was done using a 0.5:1× bead: sample volume, followed by left sided size selection with a 1:1× bead:sample volume. Quality and quantity of the finished libraries were assessed using a combination of Agilent DNA High Sensitivity chip (Agilent Technologies, Inc.), QuantiFluor® dsDNA System (Promega Corp., Madison, WI, USA), and Kapa Illumina Library Quantification qPCR assays (Kapa Biosystems). Individually indexed libraries were pooled and 75 bp, paired end sequencing was performed on an Illumina NextSeq 500 sequencer using a 150 bp HO sequencing kit (v2) (Illumina Inc., San Diego, CA, USA). Base calling was done by Illumina NextSeq Control Software (NCS) v2.0 and output of NCS was demultiplexed and converted to FastQ format with Illumina Bcl2fastq2 v2.20.0.

Reads were aligned to hg19 in the same manner as described above for ChIP-seq, with the following exception, the enterobacteria phage lambda genome (NC_001416.1) was added as additional contigs. BAMs were ingested into R (v3.6.1) and processed using csaw (v1.18.0). Briefly, a 150 bp sliding window with a 50 bp step-size was used to summarize the read counts with a maximum fragment size set to 500 bp. Next, the background was estimated using a 1kb sliding window where reads were binned and summarized. Regions were excluded if they overlapped known blacklist regions in hg19. Regions having signal greater than log 2(3) fold-change over background were retained for differential accessibility analysis. Libraries were normalized using RUVg from the RUVSeq (v1.18.0) package, with the lambda reads as the control "genes" (Risso, Ngai, Speed, & Dudoit, 2014). The weights derived from a k=1 were used as an additional covariate in the linear model to test for mithramycin-mediated changes over time. PCA plots examining the effects of increasing k were plotted using EDASeq (v2.18.0) (Risso, Schwartz, Sherlock, & Dudoit, 2011). Differentially accessible regions (DAR) were computed by fitting a similar model as described for ChIP-seq, but with the RUV weights added. Statistical significance was determined as $q<0.05$. Library complexity analysis was performed using preseqR (v4.0.0) (Deng, Daley, & Smith, 2015). Chromatin conformation was inferred by extending methods as previously described and implemented in compartmap (v1.3). Briefly, filtered read counts are summarized within a bin, pairwise Pearson correlations are computed across samples within a group, and the first principle component describes the chromatin conformation state using the sign of the eigenvalue. Chromosome-wide compartment dissimilarity scores were computed relative to solvent by calculating 1—Pearson correlations.

chromHMM Analysis. Raw ChIP-seq data was downloaded from phs000470 for 19 MRT patients and aligned to the hg38 primary assembly with bwa mem, duplicates marked and removed with samblaster, and converted to BAM format with samtools (Chun et al., 2016). The following chromatin marks were used as input to construct the chromHMM (v1.18) model: H3K4me1, H3K4me3, H3K9me3, H3K27Ac, H3K27me3, H3K36me3 (Ernst & Kellis, 2012, 2017). Additionally, matched input samples were used for local thresholding during the binarization step. BAMs were binarized using default values and segmented using the Roadmap 18-state core model (model_18_core_K27ac.txt). Segmented bed files were then lifted over to hg19 coordinates using UCSC liftover. Browser files were generated using the MakeBrowserFiles function from chromHMM for all 19 patients. The 18-state model was then collapsed into 6 "super states" for all patients. Next, the original and collapsed chromatin state calls were combined into a RaggedExperiment (v1.8.0) object in R. Differential regions were then queried for overlaps to specific chromatin super states, where a consensus state was called as having at least 50% of patient samples having the same inferred state from chromHMM. Donut plots were generated using significant ($q<0.05$) trended changes in accessibility (ATAC-seq) or binding (ChIP-seq) from 8 hours to 18 hours of mithramycin treatment, relative to solvent.

siRNA Knockdown. BT12 cells were passaged twice in RPMI-1640 medium (supplemented with 10% FBS and 2 mM glutamine) without antibiotics prior to siRNA treatment. RNAiMax Lipofectamine (3.25 µL per well in a 12-well dish) was added to siRNA targeting SMARCA4, SMARCC1, or SP1 and allowed to complex. 150,000 cells were combined with the lipid siRNA complex and incubated for 30h (SP1) or 48h (SMARCA4 and SMARCC1) before collection for qRT-PCR analysis. For live cell imaging, RNAiMax lipofectamine was decreased 1.5 µL per well in a 24-well dish and BT12 cells were decreased to 35,000 cells per well.

Luciferase Cells. CMV-luciferase plasmid (Grohar et al., 2011) was linearized with HF-Sal1 (New England Biosciences) and transfected into G401 cells using Buffer R, program 0-017, and the Amaxa Nucleofector system (Lonza). Transfected G401 cells were expanded under G418 (1 mg/mL) selection. Transfected cells were confirmed to be pathogen-free prior to in vivo experiments.

Xenograft Experiments. $5\times10^6$ G401-luc cells were injected intramuscularly into the gastrocnemius of 8 to 10-week-old female homozygous nude mice (Crl; Nu-Foxn1$^{Nu}$). Tumor growth was monitored by caliper measurement and tumors grew 14 days before starting treatment (>100 mm$^3$). Mice were treated with intraperitoneal bolus injections or continuous infusion with Alzet micro-osmotic pumps (DURECT Corporation, model 1007D). Pumps were implanted intraperitoneally and removed with 7-days after end of drug delivery. Vehicle treated mice (n=10) were treated with 8 intraperitoneal injections or 7-day continuous infusion (168-hours) of PBS supplemented with magnesium and calcium. Mithramycin treated mice were treated with 1 mg/kg mithramycin IP (8 injections total, n=12), 2.4 mg/kg mithramycin in a 3-day (72-hours, n=12) or 7-day (168-hours, n=12) continuous infusion. EC-8042 treated mice were treated with 30 mg/kg EC-8042 in a 3-day (72-hour, n=12) infusion or 50 mg/kg in a 7-day (168-hour, n=12) infusion. Tumor volume was measured daily and calculated using the equation $(Dxd^2)/6\times3.12$, where D is the maximum diameter and d is the minimum diameter. All experiments were performed in accordance with and the approval of the Van Andel Institute (VAI) Institutional Animal Care and Use Committee (IACUC). Investigators were not blinded to the treatment groups.

Bioluminescence Imaging. Mice were administered Firefly D-Luciferin (GoldBio, 1.5 mg/mouse) with intraperitoneal injections. After injection anesthesia was administered throughout the image acquisition (3% isoflurane at 1 L/min 02 flow). Bioluminescent images were taken 10 minutes after injection using the AMI-1000 imaging system.

Microcomputed Tomography (micro-CT). Mineralized tissue within tumors was examined using the SkyScan 1172 micro-computed tomography (µCT) system (Bruker MicroCT, Kontich, Belgium). Tumors were scanned in 70% ethanol using an X-ray voltage of 60 kV, current of 167 µA, and 0.5 mm aluminum filter. The pixel resolution was set to 2000×1200, with an image pixel size of 8 μm. A rotation step of 0.40 degrees and 3600 scanning was used. 2D cross-sectional images were reconstructed using NRecon 1.7.4.6 (Bruker MicroCT, Kontich, Belgium). A volume of interest (VOI) was defined for each tumor using DataViewer 1.5.6.3 (Bruker MicroCT, Kontich, Belgium). A region of interest (ROI) around the tumor was defined and 3D files were generated using CTAn 1.18.8.0 (Bruker MicroCT, Kontich, Belgium). Representative 3D images were created using CTvol 2.3.2.0 (Bruker MicroCT, Kontich, Belgium).

Tissue Staining and Immunohistochemistry. Tissues were decalcified in 10% EDTA (pH 8.0) for 7-days prior to paraffin embedding. Paraffin embedded tissue was sectioned into 5-micrometer sections and mounted on colormark plus charged slides. Hematoxylin and Eosin staining was performed on the Ventana Symphony instrument. For immunohistochemistry, antigen retrieval was performed on the PT Link platform on the Dako Autostainer Plus instrument. Following blocking, tissue was incubated with H3K27me3 antibody (Abcam 1:250) or Cleaved Caspase-3 (Cell Signaling Antibody 1:250), washed and then secondary antibody (Envision+System HRP labelled polymer Anti-Rabbit, Dako 1:100) and finished with Dako Liquid DAB+Substrate Chromogen System.

Project Statistics. qPCR data is normalized to solvent (mRNA expression data) or input (ChIP data) as fold-change from 3 independent experiments performed in technical duplicate. The p-values were determined by one-way ANOVA using Dunnet test for multiple comparisons.

Example 2—Results

Mithramycin sensitivity is linked with SWI/SNF mutation or complex dysregulation. The inventors' previous screening data suggested that rhabdoid tumor (RT) cells were extremely sensitive to mithramycin and second-generation analogues (FIG. S1A) (Osgood et al., 2016). In order to confirm these findings and explore the relationship with SWI/SNF, the inventors analyzed independently published screening data of a panel of sarcoma cell lines to determine the relative sensitivity of these tumors to mithramycin (Teicher et al., 2015). Again, they found that RT cell lines were among the most sensitive cell lines (FIGS. 1A-B). Since RT cells are characterized by a single mutation, SMARCB1 deletion, the inventors looked to see if the other cell lines that were hypersensitive to the drug also had mutations in SWI/SNF. Indeed, they found that 19 of the top 25 most sensitive sarcoma cell lines have a SWI/SNF mutation or dysregulation.

In order to confirm that this sensitivity was related to molecular features of the tumor and exclude a general hypersensitivity of the tumor to non-specific chemotherapy, the inventors compared the cellular sensitivity of RT to mithramycin and chemotherapy to Ewing sarcoma cells. In contrast to RT which is resistant to chemotherapy in the clinic, Ewing sarcoma is known to be responsive to chemotherapy. The inventors found that the in vitro sensitivity pattern to chemotherapy reflects the clinical experience. Three rhabdoid tumor cell lines (BT12 AT/RT, CHLA266 AT/RT, and G401 RTK) were 70-fold, 4-fold, and 100-fold less sensitive to three broadly active chemotherapy agents, etoposide, doxorubicin, and SN38 (the active metabolite of irinotecan) than Ewing sarcoma cells (FIG. 1C). In contrast, the inventors confirmed that all three cell lines were equally sensitive to mithramycin as the Ewing sarcoma cells. These data are consistent with a striking sensitivity of mithramycin in rhabdoid tumor and correlate mithramycin sensitivity with SWI/SNF dysregulation.

Mithramycin evicts SWI/SNF from chromatin and amplifies H3K27me3 in a time-dependent manner. Due to the known sensitivity of EZH2 blockade and the known effects of mithramycin in Ewing sarcoma cells on EZH2, the inventors initially reasoned that MMA may be acting to inhibit EZH2 in rhabdoid tumor cells. In contrast, however, mithramycin treatment led to a dose-dependent increase in global H3K27me3 by 18-hours of treatment (FIG. 2A). They correlated H3K27me3 amplification with suppression of cellular proliferation and induction of apoptosis as measured by cleaved caspase induction (FIGS. 2B-C). To further demonstrate the association of apoptosis with H3K27me3 amplification, the inventors performed a time course with 100 nM mithramycin in BT12 RT cells (FIG. 2D). Treatment with 100 nM mithramycin led to amplification of H3K27me3 in a time-dependent fashion that correlated with cleavage of PARP by 8-hours of exposure. They further validated time-dependent H3K27me3 amplification at specific loci with chromatin immunoprecipitation. In a time-dependent manner, H3K27me3 occupancy increases at MYT1, a well-established PRC2 target, and CCND1, a cell cycle progression gene (FIG. 2E). Here, GAPDH is the locus control and H3K27me3 occupancy was not affected with drug treatment (FIG. S1B). It is notable that compared to non-malignant brain tissue, AT/RT tumors have much lower global H3K27me3 (Erkek et al., 2019). Therefore, it is likely that the tumor has compensated for the loss of SMARCB1. It follows that amplification of the imbalance between SWI/SNF and PRC2 would therefore be detrimental to rhabdoid tumor survival and an important therapeutic vulnerability.

The inventors have previously shown amplification of H3K9me3 and H3K27me3 as a result of SWI/SNF eviction in Ewing sarcoma cells following treatment with a DNA minor groove binding compound (Harlow et al., 2019). They therefore hypothesized that mithramycin might evict of SWI/SNF from chromatin to drive a similar cellular response in RT cells. The inventors treated rhabdoid tumor cells with three exposures of 100 nM mithramycin (1-hour, 8-hours, and 18-hours) then biochemically fractionated the cells into chromatin bound or soluble fractions. Consistent with the inventors' hypothesis, mithramycin evicts SWI/SNF from chromatin by 8-hours of 100 nM exposure (FIG. 2F). Interestingly, this effect also occurred in G401, a rhabdoid tumor of the kidney cell line, but was not seen in U20S, an osteosarcoma cell line with wild type SWI/SNF suggesting some selectivity of this effect for mutant SWI/SNF (FIGS. 2G-H). It is notable that both mithramycin and SWI/SNF bind the minor groove of DNA and therefore mithramycin may be competitively evicting SWI/SNF from chromatin (Quinn, Fyrberg, Ganster, Schmidt, & Peterson, 1996; Sastry & Patel, 1993). The inventors confirmed loss of SWI/SNF from chromatin with ChIP-qPCR of SMARCC1, an essential SWI/SNF subunit, at multiple loci. In a time-dependent manner, SMARCC1 occupancy decreases at MYT1 and CCND1 relative to GAPDH (FIG. 2I, FIG. S1B).

Lastly, the inventors confirmed the relationship of SWI/SNF and PRC2 to mithramycin sensitivity with siRNA genetic knockdown. SMARCA4 and SMARCC1, two SWI/SNF subunits, as well as EZH2 were knocked down with siRNA for 48-hours before being treated with mithramycin. SWI/SNF knockdown sensitizes BT12 rhabdoid tumor cells to mithramycin while EZH2 loss confers resistance (FIG.

2J). These data provide further evidence that SWI/SNF and PRC2 are a critical therapeutic axis for mithramycin sensitivity in rhabdoid tumor.

Mithramycin evicts SWI/SNF from the SP1 promoter decreasing expression providing a mechanism for mithramycin-dependent SP1 inhibition. Mithramycin is widely regarded as a competitive SP1 inhibitor based on gel shift data and chromatin immunoprecipitation studies. These data show loss of SP1 binding at target genes (Remsing et al., 2003; Snyder, Ray, Blume, & Miller, 1991). To further investigate the role of SP1 in rhabdoid tumor, the inventors quantified the expression of SP1 following mithramycin treatment. Using quantitative PCR and western blot, they found that SP1 expression decreases in a time-dependent manner in rhabdoid tumor cells consistent with other reports in other cell lines (FIGS. 3A-B). Due to the loss of SP1 expression, the inventors reasoned mithramycin may be working by an epigenetic mechanism to silence SP1 expression. Loss of SP1 expression was recapitulated with siRNA knockdown of two SWI/SNF subunits, SMARCC1 and SMARCA4 (FIG. 3C). They hypothesized that SWI/SNF eviction following mithramycin treatment may be the mechanism of SP1 repression. The inventors performed ChIP-qPCR for SMARCC1 occupancy in the SP1 promoter. Here, SMARCC1 decreases in a time-dependent manner relative to the IgG and GAPDH controls (FIG. 3D, FIG. S1B). Strikingly, H3K27ac decreased in parallel with the loss of SMARCC1 occupancy, while H3K27me3 accumulated in the SP1 promoter (FIGS. 3E-F). These data indicate the effect of mithramycin on SP1 activity occurs at the SP1 promoter through eviction of SWI/SNF. In order to determine if SP1 is a therapeutic vulnerability in RT cells and responsible for the sensitivity of this tumor type to mithramycin, the inventors treated BT12 and G401 cells with tolfenamic acid, a non-steroidal anti-inflammatory that degrades active SP1 protein. However, despite a loss of SP1 expression, rhabdoid tumor cells were not sensitive to tolfenamic acid (FIGS. 3G-H). SP1 knockdown with siRNA confirmed that SP1 loss did not impact BT12 cell viability (FIG. S1C). Cumulatively, these data indicate SP1 loss is not the primary driver of mithramycin sensitivity in rhabdoid tumor.

Mithramycin induces epigenetic reprogramming of chromatin compartments and rhabdoid tumor promoters. In order to understand how the eviction of SWI/SNF by mithramycin drives gene expression changes that lead to this cellular hypersensitivity, the inventors looked at the impact of treatment on enhancers, promoters and overall chromatin structure genome-wide. They performed ATAC and ChIP sequencing following solvent, 8-hours, and 18-hours of 100 nM mithramycin treatment in BT12 rhabdoid tumor cells. To quantify chromatin remodeling following mithramycin treatment, the inventors developed novel spike-in controls for the ATAC sequencing. First, lambda phage was added during the transposition reaction to quantify the efficiency of the Tn5 tagmentation. Here, lambda phage tagmentation will be equivalent across all treatments and the lambda phage reads were utilized as a normalization for library complexity (FIGS. S2A-D). Second, three phiX DNA fragments were designed with equal nucleotide distribution and ligated Tn5 adapters. phiX DNA fragments were mixed equimolar and introduced during library amplification to normalize for nucleotide bias during PCR amplification. In order to correlate accessibility with active promoters and enhancers, the inventors performed ChIP-sequencing with H3K27ac. The lambda phage read depth from the ATAC-seq was used to normalize the H3K27ac sequencing libraries.

To gain insight into the magnitude and genome wide distribution of chromatin accessibility changes following mithramycin treatment, the inventors quantified the number of significant regions (q-value<0.05) with increased or decreased H3K27ac and accessibility for each chromosome (FIG. 4A). Overall, the distribution of H3K27ac and accessible chromatin across the genome was relatively uniform. Further, regions that were increasing or decreasing at 8-hours of mithramycin treatment continue to trend in that direction at 18-hours mithramycin treatment. Finally, the inventors correlated those changes with peaks at the transcriptional start site and not distal intergenic regions (FIG. 4B; FIG. S3A-H).

In order to better understand how these changes correlate with transcriptional changes, the inventors explored how these changes correlate with A/B chromatin compartments (FIG. 4C). In this case, they found a more focal and dynamic pattern of compartment reorganization. Specific chromosomes (chr 20, 22, 14) showed substantial changes in A/B compartment organization. Compartment remodeling is much more dynamic than the region changes in FIG. 4A. Here, chromosomes trend in dissimilarity to solvent from 8-hours to 18-hours mithramycin treatment (e.g., chr1, 3-9, 13, 17, 18, 20, 22) while other chromosomes trend back toward solvent similarity by 18-hours mithramycin treatment (e.g., chr 2, 10-12, 14-16, 19, 21, X). Strikingly, for chromosomes that did not have large region differences (e.g., chr20 and chr22) (FIG. 4A), these chromosomes exhibited compartment remodeling with mithramycin treatment (FIG. 4C). These data indicate that mithramycin treatment leads to both changes in the number of differentially bound and accessible regions as well as compartment remodeling in the absence of regional accessibility changes.

In order to understand how these changes in compartments influence the chromatin states specific to rhabdoid tumor, the inventors developed chromHMM tracks from primary malignant rhabdoid tumors sequenced in TARGET and correlated it to the ATAC and ChIP-sequencing data (FIG. 4D). They initially utilized the 18-state model but collapsed these states into six super-states for functional analysis. The inventors overlaid the differentially bound H3K27ac ChIP-seq and differentially accessible ATAC-seq with the chromHMM super-states to elucidate how mithramycin reprograms the genome specific to rhabdoid tumor. Again, they found evidence of compartment remodeling with the largest percentage of DARs being in heterochromatin and repetitive elements (FIG. 5E). Due to the established relationship of SWI/SNF to enhancers, the inventors hypothesized that mithramycin would lead to rewiring of the enhancers. However, while 480 of the trended differentially bound H3K27ac ChIP-seq peaks aligned with enhancer states, 2281 peaks overlaid rhabdoid tumor promoters (184 of which are active or bivalent promoters). These peaks correlated with 75% of the trended DBRs that increase in the H3K27ac ChIP-seq mapped to the promoters while 30% of promoters decreased. The trended differentially accessible ATAC-seq peaks were divided among enhancer (661), promoter (172) and transcribed (1912) regions. Nevertheless, these data indicate mithramycin primarily remodels rhabdoid tumor promoters and gene bodies rather than enhancers.

Promoter reprogramming correlated with RNA-sequencing of mithramycin at 8-hour and 18-hours (FIGS. 4F-G). Volcano plot analysis of genes that meet a 2 log FC and 10e-5 q-value cut off show an increase in the number of up-regulated genes at 8-hours (210 genes) compared to 18-hours (368 genes). Similarly, this threshold shows a large decrease in the number of genes down-regulated at 8-hours (615 genes) compared to 18-hours (49 genes). The inventors analyzed these gene expression changes with functional pathway enrichment (Yu & He, 2016). Chromatin modifying enzymes and chromatin organization are among the top pathways down-regulated at 8-hours mithramycin treatment while PRC2 methylation of histones is one of the top pathways up-regulated at 18-hours (FIGS. S4A-B). Enrichment of these pathways in the gene expression data provide further evidence for mithramycin disrupting SWI/SNF and PRC2 dynamics in rhabdoid tumor. Finally, the inventors correlated gene expression changes with transcription factor consensus motifs (FIG. 4H). ETS is the top up-regulated motif which is known to be associated with SWI/SNF (Boulay et al., 2017). YY1, a DNA minor groove binding transcription factor, is the top down-regulated motif which is consistent with the idea that mithramycin remodels chromatin compartments to reprogram enhancer-promoter loops and gene expression (Weintraub et al., 2017). Importantly, while YY1 regulates pluripotency and blocks multiple differentiation programs, the ETS transcription factor family are pioneer transcription factors that drive differentiation. Thus, it is probable that mithramycin-dependent epigenetic and transcriptional reprogramming may lead to differentiation.

SWI/SNF inhibition by mithramycin drives divergent phenotypes in rhabdoid tumor cells. In order to link these chromatin changes that occur with treatment to a defined cellular phenotype, the inventors integrated the RNA-seq, ATAC-seq, and H3K27ac ChIP-seq in order to perform multi-omic analysis and identify gene expression changes that are associated with specific changes in promoter accessibility and activation. Analysis of genes that had at least a 1 log FC increase or decrease at both 8-hours and 18-hours mithramycin treatment for gene expression and chromatin accessibility led to 54 common genes up-regulated and 25 common genes down-regulated that changed in accessibility and H3K27ac in the appropriate direction (FIG. 5A, FIG. S4C). Gene ontology analysis of the most significant enriched processes in the 54 up-regulated genes were related to cell death and apoptosis (FIG. 5A). In contrast, no processes were significantly enriched in the 25 down-regulated genes which aligns with the loss of down-regulated RNA-seq genes by 18-hours mithramycin treatment described in FIG. 4G. Three of the up-regulated gene targets BCL10 (pro-apoptotic), BTG2 (pro-apoptotic), and CDKN1A (cell cycle) all exhibited large peaks in the transcriptional start sites of the genes rather than enhancers providing further evidence of mithramycin promoter reprogramming (FIG. 5B, FIG. S4D). Importantly, GSEA analysis of the genes up-regulated from the RNA-seq highlights cell death and apoptosis by 8-hours of mithramycin treatment (FIG. 5C). This result was confirmed in vitro with live cell imaging and proliferation analysis. The inventors performed a time-course of 100 nM mithramycin treatment in BT12 and G401 cells (FIG. 5D, FIG. S4E). After the indicated time, the cell media was replaced with drug-free media. After 8-hours of exposure with 100 nM mithramycin, the proliferation of BT12 and G401 cells was suppressed and the phenotype is indicative of cell death (FIG. 5E, FIG. S4F). Interestingly, with decreasing concentrations of mithramycin, the cells remained growth arrested consistent with the described $IC_{50}$ (FIG. 5F). However, at these lower concentrations, the cells showed a very different phenotype with evidence of mesenchymal differentiation, the appearance of lipid accumulation and even the presence of mature adipocytes by 24 hours of exposure to 20 nM mithramycin (FIG. 5G). These changes were also evident in the inventors' RNA sequencing data as GSEA analysis of a stem cell differentiation gene list shows enrichment of this signature by 8-hours of mithramycin treatment (FIG. 5H). Functional GSEA showed that 10 out of 12 pathways previously independently identified as aberrantly activated in primary AT/RT were associated with a differentiation gene signature and significantly downregulated in the inventors' RNA sequencing data (FIGS. 5I-J). These data indicate that the cellular phenotype of growth suppression by mithramycin is exposure dependent and varies by concentration and time of exposure from an apoptotic phenotype at transient high-concentration exposures while a lower concentration using continuous exposure leads to a mesenchymal differentiation phenotype.

Mithramycin shows activity in an intramuscular rhabdoid tumor xenograft. In order to determine which of the exposures (transient high-concentration or continuous) is more effective in this tumor type, the inventors directly compared these exposures in vivo in an intramuscular xenograft mouse model of rhabdoid tumor with G401 cells. They chose an intramuscular model to exclude limitations on the CNS penetration of the drug and to model the sarcoma variant of the tumor, MRT. In addition, a renal capsular model showed erratic growth (data not shown). Mice were implanted with tumors which were allowed to establish to a minimum of 100 $mm^3$. Mice were treated with either 1 mg/kg intraperitoneal injection three times per week (every other day) for 2 weeks to model the transient high-dose exposure or as continuous infusion of only 2.4 mg/kg given over 3 days via an osmotic pump to model the lower concentration continuous exposure. Bolus injection of mithramycin showed limited suppression of tumor growth (FIG. 6A). In contrast, mice treated with a continuous infusion of mithramycin led to a more pronounced suppression of tumor growth, including a regression of a tumor that was 500 $mm^3$ at the start of treatment (FIG. 6B). These effects translated into suppression of tumor growth across the cohort of mice that favored those treated with continuous infusion (FIG. 5C). In addition, the growth suppression persisted for almost 2 weeks after discontinuing treatment. Re-treatment was not possible due to IACUC limitations against additional surgery to implant another set of drug eluting pumps and all tumors recurred. In addition, the inventors could not escalate the dose further because of toxicity. Importantly, however, continuous infusion recapitulated the mechanism of growth suppression described in vitro. There was a marked increase in H3K27me3 staining that correlated with apoptosis as measured by cleaved caspase 3 (CC3) staining (FIGS. 6D-E). It is notable that this correlation was observed in vitro (see FIGS. 2C-D). There was limited evidence of differentiation with the parent compound.

EC-8042, a less toxic mithramycin analogue, leads to marked tumor regression and mesenchymal differentiation in vivo. In an effort to improve the activity of mithramycin and increase the clinical relevance of the described effects, the inventors next evaluated a less toxic mithramycin analogue EC-8042 in this model. EC-8042 is a second generation mithramycin analogue that is more than 10 times less toxic than mithramycin in multiple species but preserves the activity of mithramycin (Osgood et al., 2016). Rhabdoid tumor is sensitive to EC-8042 treatment at a slightly higher concentration as mithramycin and induces the described mesenchymal differentiation phenotype in vitro (FIGS. S5A-B). This is consistent with the similarity between mithramycin and EC-8042 in other models in all aspects except toxicity (Osgood et al., 2016). Mice with rhabdoid tumor xenografts were treated with 3-days or 7-days continuous infusion of EC-8042 for a total dose of 30 mg/kg or 50 mg/kg, respectively. All mice in both cohorts experienced striking regressions of their well-established tumors including many with large tumors >400 $mm^3$ (FIGS. 7A-B). Bioluminescent imaging in a subset of mice showed almost no detectable tumor at the end of infusion (FIG. 7C). Again, retreatment was not possible due to IACUC limitations on a second pump implantation surgery. Nevertheless, in most mice the response was durable lasting almost 6 weeks post end of infusion (FIG. 7D). Importantly, several mice were cured of their disease and never showed tumor recurrence 140 days after treatment (FIG. 7E). The mice experienced minimal transient weight loss that resolved with cessation of drug infusion (FIG. S5C).

The tissue once again showed that the described mechanism was achieved in these mice. In a time-dependent manner, global H3K27me3 was amplified, while global H3K27ac was decreased (FIGS. 8A-B, FIG. S6A). The intense staining of H3K27me3 was not present in day 8, but it is notable that the tumors have regressed and the mitochondrial stain for human cells did not identify any tumor cells (FIG. 8C, FIG. S6A). Amplification of H3K27me3 positively correlated with cleaved caspase3 and reduction of Ki67 indicating suppression of proliferation and induction of apoptosis (FIG. 8D, FIGS. S6A-B). Importantly, the positive correlation of H3K27me3 and CC3 was also exhibited with mithramycin treatment.

Finally, consistent with the in vitro phenotype, the tumors showed striking evidence of mesenchymal differentiation. In contrast to the in vitro data which favored an adipogenic lineage, the tumors showed evidence of differentiation into bone with the appearance of trabecular-like ossification as well as cartilage and adipocytes (FIG. 8E). The presence of osteoblasts and embedded osteocytes in the trabecular architecture provides further support for EC-8042 inducing osteogenesis (FIG. S6C). In addition, principal component analysis of mithramycin treated BT12 cells with gene signatures from bone shows mithramycin treatment clusters with normal skull compared with solvent and it is notable that Wnt3 was one of the top promoters remodeled after mithramycin treatment (FIG. S6D, data not shown). The inventors confirmed calcification of the tumor tissue with microcomputed tomography (micro-CT). Here, EC-8042 treatment enhances the calcification and mineralization of rhabdoid tumor xenografts compared with vehicle (FIG. 8E). The appearance of a mesenchymal differentiation phenotype is supported by rhabdoid tumor cell of origin studies indicating a mesenchymal or neural crest origin and clinical evidence supporting mesenchymal features in patients (Rorke, Packer, & Biegel, 1996). The differentiation phenotype is not fully penetrant and is represented by mixed lineage, likely due to transcriptional and epigenetic heterogeneity in the xenograft as well as influences of the micro-environment. Nevertheless, this phenotype leads to a significant increase in survival of the rhabdoid tumor xenografts treated with EC-8042.

Figure 10:
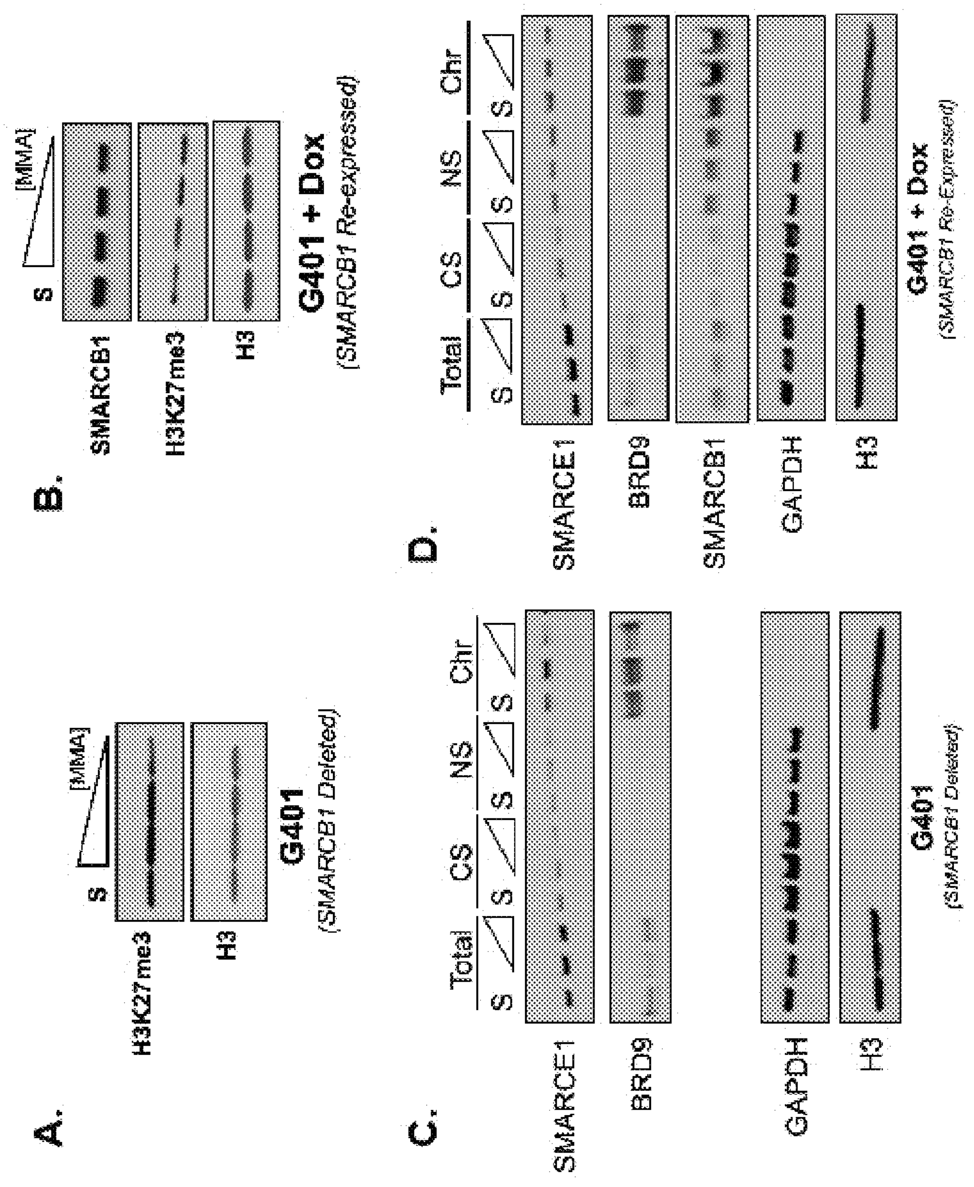
FIGS. 10A-D. SWI-SNF eviction and H3K27me3 accumulation is dependent on SMARCB1-deletion in rhabdoid tumor cells.

In order to link mithramycin-mediated eviction of SWI/SNF binding and accumulation of H3K27me3 to the described cellular hypersensitivity of this particular cell type, the inventors next examined the importance of SMARCB1 deletion to these effects. Indeed, these effects were dependent on deletion of SMARCB1 as complementation using a doxycycline inducible SMARCB1 eliminated the dose dependent accumulation of H3K27me3 seen with mithramycin exposure in G401 cells (FIGS. 10A-B). Chromatin fractionation in G401 cells again showed a loss of SWI/SNF binding to the genome (FIG. 10C). Further, complementation of these cells with the same inducible SMARCB1 that eliminated H3K27me3 accumulation also led to the inability of mithramycin to compete SWI/SNF off chromatin with restoration of SMARCB1 expression consistent with the need for the deletion for this activity (FIG. 10D). These data are consistent with the described mechanism of action for mithramycin being dependent on SMARCB1-deletion and SWI/SNF mutation.

Example 3—Discussion

In this study, the inventors identify mithramycin as a direct inhibitor of the SWI/SNF chromatin remodeling complex. They show eviction of SWI/SNF from chromatin and the induction of a striking cellular response characterized by chromatin compartment remodeling, a change in the location and distribution of H3K27ac and differential changes in chromatin accessibility that drive both an apoptotic and differentiation phenotype. This genotype and phenotype is clearly captured in vitro in modeling experiments and in a multi-omic analysis that links gene expression changes to alterations in chromatin structure and accessibility. Importantly, the epigenetic reprogramming favors regions near the transcriptional start site and not long-range enhancers. Together, these effects explain the striking sensitivity of this tumor to this drug and provides a new therapeutic option for these notoriously chemo-refractory patients, particularly with the less-toxic analogue EC-8042.

This study now represents the second example of SWI/SNF eviction inducing a cellular response characterized by widespread changes in histone post-translational modifications and chromatin remodeling (Harlow et al., 2019). In both cases, the compounds were originally identified as inhibitors of the EWS-FLI1 transcription factor, which has been shown to depend on SWI/SNF in other studies (Boulay et al., 2017). It is likely that this specific response to the release of the aberrant distribution of SWI/SNF in both tumor types accounts for the heightened sensitivity of these tumors to these compounds. It is tempting to speculate that these compounds would therefore be active in the 20% of tumors characterized by aberrant SWI/SNF activity as suggested by the inventors' in vitro screening data.

Importantly, in addition to a new therapeutic option, this study provides important insight into the biology of RT. It has been suggested that the loss of SMARCB1 leads to a SWI/SNF complex that binds to chromatin with lower affinity and is distributed aberrantly throughout the genome. Consistent with this idea, the inventors have identified a small molecule that is able to inhibit oncogenic SWI/SNF with some selectivity relative to wild-type. They show that the eviction of SWI/SNF only occurs in RT cells and not in SWI/SNF wild-type U2OS cells. In addition, the toxicity profile, particularly for EC-8042, demonstrates a favorable therapeutic window. This suggests effects on the tumor cells but not on the normal cells which are known to possess wild-type SWI/SNF.

Interestingly, in this study the inventors show a striking schedule dependence of these tumors for both mithramycin and EC-8042. They demonstrate that both compounds are more effective as a continuous infusion that is able to induce both an apoptotic and a differentiation endpoint of therapy. With mithramycin, this endpoint is exposure dependent where transient high concentration exposures common in the clinic favor apoptosis while low concentrations over time favor differentiation. It is only with these exposures, that the induction of H3K27me3 and loss of H3K27ac is achieved. It is an important observation that the high-concentration, transient exposure that drives the apoptotic phenotype is less effective in the xenografts than the continuous infusion. In addition, only the continuous infusion induces durable responses and even complete cures. This is consistent with clinical observations. In the case where differentiation agents have been identified in a number of tumors, these tend to be extremely active in patients with the best examples being arsenic and ATRA for APL, trabectedin for myxoid liposarcoma, and retinoids for neuroblastoma (Flynn et al., 1983; Forni et al., 2009; Sidell, Altman, Haussler, & Seeger, 1983). Furthermore, these observations provide a biomarker of activity. The induction of H3K27me3 and loss of H3K27ac staining of the FFPE tumor tissue was quite striking and only occurred in tumors that responded to the drug.

Finally, this study provides important insight into the mechanism of mithramycin. Mithramycin was originally identified as an anti-cancer agent in the 1950's. While it showed some activity in the clinic and, in particular, in testicular cancer and Ewing sarcoma, it fell out of favor due to its narrow toxicity profile. It has always been referred to as an SP1 inhibitor with recent activity suggesting activity against ETS transcription factors and EWS-FLI1, the oncogenic driver of Ewing sarcoma. The data in this study suggests that, at least in these cells, the activity against SP1 is the result of SWI/SNF blockade and not the primary mechanism of action. This is important because it allows the identification of more effective analogues, such as EC-8042, for Ewing sarcoma and other tumors that are sensitive to this class of compounds. In addition, in tumors dependent on SP1, it provides insight into approaches to develop novel combination therapies that perhaps amplify the targeting of SP1.

Together these data provide important insight into the biology and therapeutic targeting of SWI/SNF, a novel therapeutic option for the notoriously chemo-refractory rhabdoid tumor and mechanistic insight into mithramycin analogues that has the potential to impact a broad range of cancers characterized by dysregulation of SWI/SNF.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 5,538,880
U.S. Pat. No. 5,928,906
"Antibodies: A Laboratory Manual," Cold Spring Harbor Press, Cold Spring Harbor, NY, 1988.
Abbondanzo et al., *Am. J. Pediatr. Hematol. Oncol.,* 12(4), 480-489, 1990.
Allred et al., *Arch. Surg.,* 125(1), 107-113, 1990.
Ausubel et al., *Current Protocols in Molecular Biology*, Greene Publishing Associates and Wiley Interscience, N.Y., 1994.
Brown et al., *J. Immunol. Meth.,* 12; 130(1):111-121, 1990.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
De Jager et al., *Semin. Nucl. Med.* 23(2), 165-179, 1993.
Doolittle and Ben-Zeev, *Methods Mol. Biol.,* 109, 215-237, 1999.
Goding, In: *Monoclonal Antibodies: Principles and Practice,* 2d ed., Orlando, Fla., Academic Press, 60-61, 65-66, 71-74, 1986.
Gulbis and Galand, *Hum. Pathol.* 24(12), 1271-1285, 1993.
Kohler and Milstein, *Eur. J. Immunol.,* 6, 511-519, 1976.
Kohler and Milstein, *Nature,* 256, 495-497, 1975.
Nakamura et al., In: *Enzyme Immunoassays: Heterogeneous and Homogeneous Systems*, Chapter 27, 1987.
Remington's Pharmaceutical Sciences, $15^{th}$ Ed., 33:624-652, 1990.
Sambrook et al., In: *Molecular cloning: a laboratory manual,* $2^{nd}$ Ed., Cold Spring Harbor Laboratory Press, Cold Spring Harbor, NY, 1989.
Amemiya et al. (2019). *Scientific Reports,* 9(1), 9354. doi:10.1038/s41598-019-45839-z
Boulay et al. (2017). *Cell,* 171(1), 163-178.e119. doi:10.1016/j.cell.2017.07.036
Brennan et al. (2013). *Lancet Oncol,* 14(8), e329-336. doi:10.1016/s1470-2045(13)70088-3
Chun et al. (2016). *Cancer Cell,* 29(3), 394-406. doi:10.1016/j.ccell.2016.02.009
Corces et al. (2017). *Nat Methods,* 14(10), 959-962. doi:10.1038/nmeth.4396
Deng et al. (2015). *Quant Biol,* 3(3), 135-144. doi:10.1007/s40484-015-0049-7
Dobin et al. (2013). *Bioinformatics,* 29(1), 15-21. doi:10.1093/bioinformatics/bts635
Erkek et al. (2019). *Cancer Cell,* 35(1), 95-110.e118. doi:10.1016/j.ccell.2018.11.014
Ernst & Kellis (2012). *Nat Methods,* 9, 215. doi:10.1038/nmeth.1906
Ernst & Kellis (2017). *Nature Protocols,* 12, 2478. doi:10.1038/nprot.2017.124
Faust & Hall (2014). *Bioinformatics,* 30(17), 2503-2505. doi:10.1093/bioinformatics/btu314
Flynn et al. (1983). *Blood,* 62(6), 1211-1217.
Forni et al. (2009). *Mol Cancer Ther,* 8(2), 449-457. doi:10.1158/1535-7163.Mct-08-0848
Ginn & Gajjar (2012). *Front Oncol,* 2, 114. doi:10.3389/fonc.2012.00114
Grohar et al. (2011). *J Natl Cancer Inst,* 103(12), 962-978. doi:10.1093/jnci/djr156
Harlow et al. (2019). *Clin Cancer Res,* 25(11), 3417-3429. doi:10.1158/1078-0432.Ccr-18-3511
Kadoch et al. (2017). *Nat Genet,* 49(2), 213-222. doi:10.1038/ng.3734

Kia et al. (2008). *Mol Cell Biol,* 28(10), 3457-3464. doi:10.1128/mcb.02019-07

Knutson et al. (2013). *Proc Natl Acad Sci USA,* 110(19), 7922-7927. doi:10.1073/pnas.1303800110

Law et al., (2014). *Genome Biol,* 15(2), R29. doi:10.1186/gb-2014-15-2-r29

Li et al. (2009). *Bioinformatics,* 25(16), 2078-2079. doi:10.1093/bioinformatics/btp352

Lun, & Smyth (2014). *Nucleic Acids Res,* 42(11), e95. doi:10.1093/nar/gku351

Lun & Smyth (2016). *Nucleic Acids Res,* 44(5), e45. doi:10.1093/nar/gkv1191

Michel et al. (2018). *Nat Cell Biol,* 20(12), 1410-1420. doi:10.1038/s41556-018-0221-1

Nakayama et al. (2017). *Nat Genet,* 49(11), 1613-1623. doi:10.1038/ng.3958

Osgood et al. (2016). *Clin Cancer Res,* 22(16), 4105-4118. doi:10.1158/1078-0432.Ccr-15-2624

Quinn et al. (1996). *Nature,* 379(6568), 844-847. doi:10.1038/379844a0

Remsing et al. (2003). *Biochemistry,* 42(27), 8313-8324. doi:10.1021/bi034091z

Risso et al. (2014). *Nature Biotechnology,* 32, 896. doi:10.1038/nbt.2931

Risso et al. (2011). *BMC Bioinformatics,* 12(1), 480. doi:10.1186/1471-2105-12-480

Ritchie, et al. (2015). *Nucleic Acids Res,* 43(7), e47. doi:10.1093/nar/gkv007

Robinson et al. (2010). *Bioinformatics,* 26(1), 139-140. doi:10.1093/bioinformatics/btp616

Robinson & Oshlack (2010). *Genome Biol,* 11(3), R25. doi:10.1186/gb-2010-11-3-r25

Rojas-Pena et al. (2014). *J Genomics,* 2, 121-130. doi:10.7150/jgen.8833

Rorke et al. (1996). *J Neurosurg,* 85(1), 56-65. doi:10.3171/jns.1996.85.1.0056

Sastry & Patel (1993). *Biochemistry,* 32(26), 6588-6604. doi:10.1021/bi00077a012

Sergushichev, A. A. (2016). *bioRxiv,* 060012. doi:10.1101/060012

Sidell et al. (1983). *Exp Cell Res,* 148(1), 21-30. doi:10.1016/0014-4827(83)90184-2

Snyder et al. (1991). *Biochemistry,* 30(17), 4290-4297. doi:10.1021/bi00231a027

Teicher et al. (2015). *Mol Cancer Ther,* 14(11), 2452-2462. doi:10.1158/1535-7163.Mct-15-0074

Versteege et al. (1998). *Nature,* 394(6689), 203-206. doi:10.1038/28212

Wang et al. (2017). *Nat Genet,* 49(2), 289-295. doi:10.1038/ng.3746

Wang et al. (2009). *Cancer Res,* 69(20), 8094-8101. doi:10.1158/0008-5472.Can-09-0733

Wang et al. (2019). *Nat Commun,* 10(1), 1881. doi:10.1038/s41467-019-09891-7

Weintraub et al. (2017). *Cell,* 171(7), 1573-1588.e1528. doi:10.1016/j.cell.2017.11.008

Wilson et al. (2010). *Cancer Cell,* 18(4), 316-328. doi:10.1016/j.ccr.2010.09.006

Yu & He (2016). *Mol Biosyst,* 12(2), 477-479. doi:10.1039/c5mb00663e

---

What is claimed:

1. A method of treating a subject having a rhabdoid cancer or a breast cancer that exhibits a mutation in the SWI-SNF pathway comprising:

(a) determining, prior to treating, that said subject has a SMARCB1-mutated cancer; and (b) administering to said subject a EC-8042.

2. The method of claim 1, further comprising treating said subject with a second cancer therapy.

3. The method of claim 2, wherein said second cancer therapy is chemotherapy, radiotherapy, immunotherapy, hormonal therapy, toxin therapy or surgery.

4. The method of claim 1, wherein the rhabdoid cancer or breast cancer exhibits a mutation in SMARCB1.

5. The method of claim 1, wherein determining comprises:

(a) obtaining a cancer tissue sample from said subject that contains protein and/or nucleic acids; and (b) determining mutation status of an SMARCB1 protein or nucleic acid encoding SMARCB1 in said sample.

6. The method of claim 5, wherein determining comprises a nucleic acid-based assay.

7. The method of claim 5, wherein determining comprises a protein-based assay.

8. The method of claim 1, wherein said subject is a human subject.

9. The method of claim 1, wherein said subject is a non-human primate.

10. The method of claim 1, wherein said subject has previously been diagnosed with a rhabdoid cancer or a breast cancer.

11. The method of claim 1, wherein said rhabdoid cancer or breast cancer is recurrent, primary, metastatic or multi-drug resistant.

12. The method of claim 1, wherein EC-8042 is administered more than once.

* * * * *

SEQUENCE LISTING

```
<160> NUMBER OF SEQ ID NOS: 2

<210> SEQ ID NO 1
<211> LENGTH: 376
<212> TYPE: PRT
<213> ORGANISM: Homo sapiens

<400> SEQUENCE: 1

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Asp His Gly Tyr Thr Thr Leu Ala Thr Ser Val Thr
65                  70                  75                  80

Leu Leu Lys Ala Ser Glu Val Glu Glu Ile Leu Asp Gly Asn Asp Glu
                85                  90                  95

Lys Tyr Lys Ala Val Ser Ile Ser Thr Glu Pro Pro Thr Tyr Leu Arg
            100                 105                 110

Glu Gln Lys Ala Lys Arg Asn Ser Gln Trp Val Pro Thr Leu Pro Asn
        115                 120                 125

Ser Ser His His Leu Asp Ala Val Pro Cys Ser Thr Thr Ile Asn Arg
    130                 135                 140

Asn Arg Met Gly Arg Asp Lys Lys Arg Thr Phe Pro Leu Cys Phe Asp
145                 150                 155                 160

Asp His Asp Pro Ala Val Ile His Glu Asn Ala Ser Gln Pro Glu Val
```

-continued

```
                165                 170                 175

Leu Val Pro Ile Arg Leu Asp Met Glu Ile Asp Gly Gln Lys Leu Arg
            180                 185                 190

Asp Ala Phe Thr Trp Asn Met Asn Glu Lys Leu Met Thr Pro Glu Met
        195                 200                 205

Phe Ser Glu Ile Leu Cys Asp Asp Leu Asp Leu Asn Pro Leu Thr Phe
    210                 215                 220

Val Pro Ala Ile Ala Ser Ala Ile Arg Gln Gln Ile Glu Ser Tyr Pro
225                 230                 235                 240

Thr Asp Ser Ile Leu Glu Asp Gln Ser Asp Gln Arg Val Ile Ile Lys
                245                 250                 255

Leu Asn Ile His Val Gly Asn Ile Ser Leu Val Asp Gln Phe Glu Trp
            260                 265                 270

Asp Met Ser Glu Lys Glu Asn Ser Pro Glu Lys Phe Ala Leu Lys Leu
        275                 280                 285

Cys Ser Glu Leu Gly Leu Gly Gly Glu Phe Val Thr Thr Ile Ala Tyr
    290                 295                 300

Ser Ile Arg Gly Gln Leu Ser Trp His Gln Lys Thr Tyr Ala Phe Ser
305                 310                 315                 320

Glu Asn Pro Leu Pro Thr Val Glu Ile Ala Ile Arg Asn Thr Gly Asp
                325                 330                 335

Ala Asp Gln Trp Cys Pro Leu Leu Glu Thr Leu Thr Asp Ala Glu Met
            340                 345                 350

Glu Lys Lys Ile Arg Asp Gln Asp Arg Asn Thr Arg Arg Met Arg Arg
        355                 360                 365

Leu Ala Asn Thr Ala Pro Ala Trp
    370                 375
```

<210> SEQ ID NO 2
<211> LENGTH: 5164
<212> TYPE: RNA
<213> ORGANISM: Homo sapiens
<220> FEATURE:
<221> NAME/KEY: mRNA
<222> LOCATION: (1)..(5164)

<400> SEQUENCE: 2

```
gccagcgccu gcgcacugag ggcggccugg ucgucgucug cggcggcggc ggcggcugag      60

gagcccggcu gaggcgccag uacccggccc gguccgcauu ucgccuuccg gcuucgguuu     120

cccucggccc agcacgcccc ggccccgccc cagcccuccu gaucccucgc agcccggcuc     180

cggccgcccg ccucugccgc cgcaaugaug augauggcgc ugagcaagac cuucgggcag     240

aagcccguga aguuccagcu ggaggacgac ggcgaguucu acaugaucgg cuccgaggug     300

ggaaacuacc uccguauguu ccgagguucu cuguacaaga gauaccccuc acucuggagg     360

cgacuagcca cuguggaaga gaggaagaaa auaguugcau cgucacauga ucacggauac     420

acgacucuag ccaccagugu gacccuguua aaagccucgg aaguggaaga gauucuggau     480

ggcaacgaug agaaguacaa ggcugugucc aucagcacag agcccccac cuaccucagg      540

gaacagaagg ccaagaggaa cagccagugg guacccaccc ugcccaacag cucccaccac     600

uuagaugccg ugccaugcuc cacaaccauc aacaggaacc gcaugggccg agacaagaag     660

agaaccuucc cccuuugcuu ugaugaccau gacccagcug ugauccauga gaacgcaucu     720

cagcccgagg ugcugguccc cauccggcug gacauggaga ucgaugggca gaagcugcga     780

gacgccuuca ccuggaacau gaaugagaag uugaugacgc cugagauguu uucagaaauc     840
```

-continued

```
cucugugacg aucuggauuu gaacccgcug acguuugugc cagccaucgc cucugccauc    900
agacagcaga ucgaguccua ccccacggac agcauccugg aggaccaguc agaccagcgc    960
gucaucauca agcugaacau ccauguggga aacauuuccc ugguggacca guuugagugg   1020
gacaugucag agaaggagaa cucaccagag aaguuugccc ugaagcugug cucggagcug   1080
ggguugggcg gggaguuugu caccaccauc gcauacagca uccggggaca gcugagcugg   1140
caucagaaga ccuacgccuu cagcgagaac ccucugccca caguggagau ugccauccgg   1200
aacacgggcg augcggacca guggugccca cugcuggaga cucugacaga cgcugagaug   1260
gagaagaaga uccgcgacca ggacaggaac acgaggcgga ugaggcgucu ugccaacacg   1320
gccccggccu gguaaccagc ccaucagcac acggcuccca cggagcaucu cagaagauug   1380
ggccgccucu ccuccaucuu cuggcaagga cagaggcgag gggacagccc agcgccaucc   1440
ugaggaucgg guggggugg aguggggcu uccagguggc ccuucccggc acacauucca   1500
uuuguugagc cccaguccug ccccccaccc cacccucccu accccucccc agucucuggg   1560
gucaggaaga aaccuuauuu uagguugugu uuuguuuuug uauaggagcc ccaggcaggg   1620
cuaguaacag uuuuuaaaua aaaggcaaca ggucauguuc aauuucuuca acaggucaug   1680
uucaauuucu ucaaaguuuu aacauaaaaa uaaugagagc caggaguggg gccggggccu   1740
gggggacga agguggguaug ugaacaaggu uggcacacag gccucacccu ccucugccuc   1800
agauucccaa gugggcaggu gggggugaau ggggcuccgg guagcaccuc agcuccucuc   1860
agcuccccuc agccuguucu ccuuccagac ccagagagcu gagaagagua gcugugaggc   1920
ucagggcaag aggcucucug ccuuucagga acagcccuaa cccugcuccc cuugcuuggc   1980
cucaggaagg ugccgcgagc ucuccugccg ucccugggcc gcccuggcuc ugcuguguccc   2040
agauggucag gcuacugcca gcuggggccu ugcugcucug aaguccccug cggagggccc   2100
aguccugugu gggcacugcu gggcugucgc cagccugggu gcaggagggc uguucuagcu   2160
ccaguggcac ccauagccag gucagcuggg gcccuuuccc accccagcag gugcuguggc   2220
cugggccagc uccugccuua caagccagcu gugaggaaua ugggaauagc ccucccggcc   2280
uggugccagc ucuuggaguu gacacgguac agggaggaga cacagcccag ggucccuucc   2340
cagcccugcc uccaaggagu ucaugucccc ucuguucuca ucuguaauag ggaggugucc   2400
ccauucuuca gaauggacac aggaucuggg agggcagcaa acuggcucgc agcuccagcc   2460
uuacugaaga gaaugggcac agauccgggc acagauccca gcacagacug cugccacccu   2520
cagcuguugg cagguccau gcugccaggg cagggcuagg gucagaggcu gcugugcucc   2580
cuggaagugg gguagggccc cauguggggc agaggcagag cucugauuag ggauuggggu   2640
ucuuggucgc ugagauguga gaggagggcu ccuuugagca cauguuagca ugggacucuu   2700
cccagggagu uugcacucag ggccucugcc cuccaucaaa gaguggaacu ccccagagcc   2760
ccaugcacag caaggggaca gcugggccuu acuggaaggc cuugaacaaa ggggaagauu   2820
cccagcccag cugcucuuag acaugaacag guuucauugc ugagguguuu guucugucca   2880
ugagguagga accucggcaa ugaaagggug aggcagcccu gugucuccac aacugggggg   2940
auggaaggaa ccuuggcugc cucaccccac aggucgggca gggccaccug gcugggaggu   3000
gccgggaagg cugggcccuc acuccugacc gccagcucac accgccgcaa agccaucucc   3060
acaaggucug gcuacaacac ggagggcaga cucaacagag aacaguguug uuaccaugaa   3120
aaugacaacc ugucuuugga ggaggccccg ugccacugag cauccagaaa uaaaccacaa   3180
```

-continued

```
cauggacagg cuuagaacaa caaggaaagc ugccagguca gaagagaaaa augagccaca    3240

ggggucggau aaggcucaca cacguccuca gcuaaaaagg gcaggaacag aaccuuccag    3300

aagucccugc cucacccagu cucagaacuc ugcuaaggug aaaacuuagg cucugagguc    3360

auagaaaggg cagaagaccu aguccuggcc cucuucugca ccugaaucca uggggcuuug    3420

gcaucaccag augaaaaaug aggcauacgc ccaccuguca ggguggcuga ugagagacag    3480

gagaggcuag auuggcauca gccugaaggc accacuggca ggaacaucug uaggcugguu    3540

uggcacaacc uaggagacgc cuguccuggc cccagcagcc gaaaucuggu gaacuucccc    3600

gcugacuggc agguagcaga ggccuauggu gggcaggacu ugcccaaggc ccuggugggg    3660

ccaggaugag aacccugagc cugucaccug ugagcucaaa agcucugccu ggcaaccugu    3720

gagcucaaag cucugccagg caaccauggg caguuucuuu gcccucugug ggcaccccua    3780

uccuaccacc ugcaguuggg cugagaggcc acacugagug aggacggggc aggcauagaa    3840

ggauguggcc aggugagaug gggaagccag ugcugugggc caagagacug cagcucauuc    3900

uguuuauuca ggugggcccu ugcaugggcc cagccuuuag gauggguuuu uucugcccca    3960

aguagggguc auggguagga uggaagcugc cagaagccuc uuaggccugg cccugggugg    4020

gggucacugc ugcggggggug gcagaugggg uccuggcugu uccucaggga ggggcaggua    4080

auuggggucu ucugcagggg cauccaggag cagcuuucug uggggagggg cccguguuga    4140

gcacaggcca gcacaggucc ccaucggugg ggauccuucu gagggugggg agagggaggg    4200

agggcucuca acacucacag gaagccaggg gucugcagga gccucuugcc uccaggcugg    4260

uuggggaaga cguccuccag gaaguaguag auauggccca ccgcaauccc ugugagacag    4320

ccacggacug uggggucacc cuccacagcc cagaguccua gaccagcaga gccugcccca    4380

ggcccccauc cacagccugg uggcccugca ggccccacag caugagugcc ccaaagccuu    4440

gcacagagug ccagccccgg guuggccgug aaggacaagc uuaaaaggcc cagaagcagg    4500

caggacccag ggaggggagg gccugagaau aguggaggag ugggagccau ggggcaggaa    4560

cccugacccu cccauccuca cucccaucag gaccgugcaa gcaucaguag auccguccug    4620

acgaugcaaa uuaugugggc cggcuggcuu gaggggcugu aagagcacag cagcugggag    4680

ggcaggaaga uggggaugga gccaggugug aggagaacuc cagcaaggau gggagagggg    4740

ccccagggca uaagcagcgu guccugaggg gaguggccag ccuggggcgg acuagaugua    4800

ccgggaggcu cacccagcag guccacgagg auggaguugc ccagcagcag cgagaagccc    4860

augagcgccc aaggcaggaa cggugccugg aaagugagca ggccgaagaa guugacccuc    4920

acccgagggc ugcggcggcu ccacacguac accagcaugg ccaugagggc cuggcccagg    4980

aagaacaggc ugcccaggag ucccagcagc ugggccagag ucaaggugcu ccggugcagg    5040

ccucagccca agcccagggc cccucugacu ucccaagacc cuggaauucu uccccucauc    5100

uccccuaugu gcuauucccu caucaagaug agccagucca auaaaggcga cacacuccac    5160

gggc                                                                 5164
```